US011179213B2

(12) United States Patent
Huang et al.

(10) Patent No.: US 11,179,213 B2
(45) Date of Patent: Nov. 23, 2021

(54) CONTROLLERS FOR ROBOTICALLY-ENABLED TELEOPERATED SYSTEMS

(71) Applicant: Auris Health, Inc., Redwood City, CA (US)

(72) Inventors: Yanan Huang, Foster City, CA (US); Colin Allen Wilson, Burlingame, CA (US); David Stephen Mintz, Mountain View, CA (US); Jason Tomas Wilson, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 110 days.

(21) Appl. No.: 16/413,955

(22) Filed: May 16, 2019

(65) Prior Publication Data

US 2019/0350662 A1 Nov. 21, 2019

Related U.S. Application Data

(60) Provisional application No. 62/673,531, filed on May 18, 2018.

(51) Int. Cl.
*A61B 34/00* (2016.01)
*A61B 34/35* (2016.01)
*A61B 34/30* (2016.01)

(52) U.S. Cl.
CPC ........... *A61B 34/74* (2016.02); *A61B 34/35* (2016.02); *A61B 2034/301* (2016.02); *A61B 2034/742* (2016.02)

(58) Field of Classification Search
CPC ... A61B 34/74; A61B 34/35; A61B 2034/742; A61B 2034/301; A61B 34/76;
(Continued)

(56) References Cited

U.S. PATENT DOCUMENTS 4,771,262 A 9/1988 Reuss
4,896,554 A 1/1990 Culver
(Continued)

FOREIGN PATENT DOCUMENTS

EP 1 800 593 6/2007
EP 1109497 B1 * 5/2009 ............. A61B 34/30
(Continued)

OTHER PUBLICATIONS

International search report and written opinion dated Sep. 30, 2019 for PCT/US2019/32653.

*Primary Examiner* — Joseph M Dietrich
*Assistant Examiner* — Michael T. Holtzclaw
(74) *Attorney, Agent, or Firm* — Morgan, Lewis & Bockius LLP

(57) ABSTRACT

A robotically enabled teleoperated system can include a controller and an instrument capable of manipulation by the controller. The instrument can be a medical instrument. The controller can include a handle configured for actuation by an operator. The handle can be attached to a gimbal configured to allow manipulation of the handle in multiple rotational degrees of freedom. The gimbal can include a load cell. The gimbal can be configured for impedance control. The controller can also include a positioning platform coupled to the gimbal and configured to allow manipulation of the handle in multiple positional degrees of freedom. The controller can be configured for admittance control based at least in part on an output signal of the load cell in the gimbal.

20 Claims, 25 Drawing Sheets

(58) Field of Classification Search
CPC ......... A61B 34/37; A61B 34/70; A61B 34/71;
A61B 34/20; A61B 34/25; A61B 34/30;
A61B 2034/302; A61B 2034/304; A61B
2034/305; B29C 2045/4266; B25J
13/089; B60C 25/0587; F16C 2322/59
See application file for complete search history.

(56) References Cited

U.S. PATENT DOCUMENTS

| | | | |
|---|---|---|---|
| 5,008,528 | A | 4/1991 | Duchon |
| 5,176,310 | A | 1/1993 | Akiyama et al. |
| 5,280,781 | A | 1/1994 | Oku |
| 5,499,632 | A | 3/1996 | Hill et al. |
| 5,524,180 | A | 6/1996 | Wang et al. |
| 5,526,812 | A | 6/1996 | Dumoulin et al. |
| 5,762,458 | A | 6/1998 | Wang et al. |
| 5,831,614 | A | 11/1998 | Tognazzini et al. |
| 5,899,851 | A | 5/1999 | Koninckx |
| 5,963,770 | A | 10/1999 | Eakin |
| 6,007,550 | A | 12/1999 | Wang et al. |
| 6,016,439 | A | 1/2000 | Acker |
| 6,028,409 | A | 2/2000 | Wierda |
| 6,038,467 | A | 3/2000 | De Bliek et al. |
| 6,096,004 | A | 8/2000 | Meglan et al. |
| 6,424,885 | B1 | 7/2002 | Niemeyer et al. |
| 6,425,865 | B1 | 7/2002 | Salcudean et al. |
| 6,466,198 | B1 | 10/2002 | Feinstein |
| 6,468,265 | B1 | 10/2002 | Evans et al. |
| 6,490,467 | B1 | 12/2002 | Bucholz |
| 6,516,421 | B1 | 2/2003 | Peters |
| 6,684,129 | B2 | 1/2004 | Salisbury et al. |
| 6,690,964 | B2 | 2/2004 | Bieger et al. |
| 6,714,839 | B2 | 3/2004 | Salisbury et al. |
| 6,856,827 | B2 | 2/2005 | Seeley et al. |
| 7,206,627 | B2 | 4/2007 | Abovitz |
| 7,574,250 | B2 | 8/2009 | Niemeyer |
| 7,594,925 | B2 | 9/2009 | Danek |
| 7,646,161 | B2 | 1/2010 | Albu-Schaffer et al. |
| 7,747,311 | B2 | 6/2010 | Quaid, III |
| 7,843,158 | B2 | 11/2010 | Prisco |
| 7,865,266 | B2 | 1/2011 | Moll et al. |
| 7,955,322 | B2 | 6/2011 | Devengenzo et al. |
| 7,979,157 | B2 | 7/2011 | Anvari |
| 8,126,114 | B2 | 2/2012 | Naylor et al. |
| 8,137,047 | B2 | 3/2012 | Ishii et al. |
| 8,167,873 | B2 | 5/2012 | Schena |
| 8,170,716 | B2 | 5/2012 | Coste-Maniere et al. |
| 8,180,114 | B2 | 5/2012 | Nishihara et al. |
| 8,182,470 | B2 | 5/2012 | Devengenzo et al. |
| 8,343,096 | B2 | 1/2013 | Kirschenman et al. |
| 8,391,954 | B2 | 3/2013 | Quaid, III |
| 8,398,541 | B2 | 3/2013 | DiMaio et al. |
| 8,469,947 | B2 | 6/2013 | Devengenzo |
| 8,521,331 | B2 | 8/2013 | Itkowitz |
| 8,541,970 | B2* | 9/2013 | Nowlin .................. A61B 34/30 318/568.21 |
| 8,543,240 | B2 | 9/2013 | Itkowitz et al. |
| 8,620,473 | B2 | 12/2013 | Diolaiti et al. |
| 8,638,057 | B2 | 1/2014 | Goldberg et al. |
| 8,672,922 | B2 | 3/2014 | Loh et al. |
| 8,716,973 | B1* | 5/2014 | Lammertse ............ B25J 9/1694 318/671 |
| 8,718,837 | B2 | 5/2014 | Wang et al. |
| 8,761,337 | B2 | 6/2014 | Naylor et al. |
| 8,777,547 | B2 | 7/2014 | Kremerman et al. |
| 8,831,782 | B2 | 9/2014 | Itkowitz |
| 8,888,764 | B2 | 11/2014 | Devengenzo et al. |
| 8,894,634 | B2 | 11/2014 | Devengenzo et al. |
| 8,918,211 | B2 | 12/2014 | Diolaiti et al. |
| 8,971,597 | B2 | 3/2015 | Zhao et al. |
| 8,972,057 | B1 | 3/2015 | Freeman et al. |
| 8,996,169 | B2 | 3/2015 | Lightcap et al. |
| 9,043,027 | B2 | 5/2015 | Durant et al. |
| 9,084,623 | B2 | 7/2015 | Gomez et al. |
| 9,193,072 | B2 | 11/2015 | Kim et al. |
| 9,221,172 | B2 | 12/2015 | Williamson et al. |
| 9,241,767 | B2 | 1/2016 | Prisco et al. |
| 9,259,280 | B2* | 2/2016 | Au .......................... A61B 34/37 |
| 9,261,172 | B2 | 2/2016 | Solomon et al. |
| 9,278,452 | B2 | 3/2016 | Brandenberger |
| 9,283,046 | B2 | 3/2016 | Walker et al. |
| 9,314,307 | B2 | 4/2016 | Richmond et al. |
| 9,333,042 | B2 | 5/2016 | Diolaiti et al. |
| 9,339,934 | B2 | 5/2016 | Kogan |
| 9,345,544 | B2 | 5/2016 | Hourtash et al. |
| 9,375,288 | B2 | 6/2016 | Robinson et al. |
| 9,383,832 | B1 | 7/2016 | Lammertse |
| 9,498,291 | B2 | 11/2016 | Balaji et al. |
| 9,503,681 | B1 | 11/2016 | Popescu et al. |
| 9,504,604 | B2 | 11/2016 | Alvarez |
| 9,532,838 | B2 | 1/2017 | Coste-Maniere et al. |
| 9,561,019 | B2 | 2/2017 | Mihailescu et al. |
| 9,561,083 | B2 | 2/2017 | Yu et al. |
| 9,566,414 | B2 | 2/2017 | Wong et al. |
| 9,586,323 | B2 | 3/2017 | Diolaiti et al. |
| 9,616,564 | B2 | 4/2017 | Pfaff |
| 9,622,827 | B2 | 4/2017 | Yu et al. |
| 9,636,184 | B2 | 5/2017 | Lee et al. |
| 9,636,185 | B2 | 5/2017 | Quaid et al. |
| 9,662,262 | B2 | 5/2017 | Hollander et al. |
| 9,713,509 | B2 | 7/2017 | Schuh et al. |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,770,216 | B2 | 9/2017 | Brown et al. |
| 9,775,681 | B2 | 10/2017 | Quaid et al. |
| 9,788,910 | B2 | 10/2017 | Schuh |
| 9,801,686 | B2 | 10/2017 | Lightcap et al. |
| 9,820,823 | B2 | 11/2017 | Richmond et al. |
| 9,827,059 | B2 | 11/2017 | Robinson et al. |
| 9,827,061 | B2 | 11/2017 | Balaji et al. |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,943,962 | B2 | 4/2018 | Sattler et al. |
| 9,943,964 | B2 | 4/2018 | Hares |
| 9,949,749 | B2 | 4/2018 | Noonan et al. |
| 9,949,800 | B2 | 4/2018 | Prisco et al. |
| 9,955,986 | B2 | 5/2018 | Shah |
| 9,956,044 | B2 | 5/2018 | Gomez et al. |
| 9,962,228 | B2 | 5/2018 | Schuh et al. |
| 9,974,620 | B2 | 5/2018 | Namiki |
| 9,980,785 | B2 | 5/2018 | Schuh |
| 9,993,313 | B2 | 6/2018 | Schuh et al. |
| 10,010,377 | B2 | 7/2018 | Iorgulescu et al. |
| 10,016,900 | B1 | 7/2018 | Meyer et al. |
| 10,022,192 | B1 | 7/2018 | Ummalaneni |
| 10,022,871 | B2 | 7/2018 | Ogawa et al. |
| 10,028,789 | B2* | 7/2018 | Quaid .................... A61B 34/30 |
| 10,034,719 | B2 | 7/2018 | Richmond et al. |
| 10,080,576 | B2 | 9/2018 | Romo et al. |
| 10,123,843 | B2 | 11/2018 | Wong et al. |
| 10,123,846 | B2 | 11/2018 | Suresh et al. |
| 10,130,427 | B2 | 11/2018 | Tanner et al. |
| 10,130,429 | B1 | 11/2018 | Weir |
| 10,136,949 | B2 | 11/2018 | Felder et al. |
| 10,136,959 | B2 | 11/2018 | Mintz et al. |
| 10,145,747 | B1 | 12/2018 | Lin et al. |
| 10,149,720 | B2 | 12/2018 | Romo |
| 10,159,532 | B1 | 12/2018 | Ummalaneni et al. |
| 10,159,533 | B2 | 12/2018 | Moll et al. |
| 10,169,875 | B2 | 1/2019 | Mintz et al. |
| 10,206,746 | B2 | 2/2019 | Walker et al. |
| 10,219,874 | B2 | 3/2019 | Yu et al. |
| 10,231,793 | B2 | 3/2019 | Romo |
| 10,231,867 | B2 | 3/2019 | Alvarez et al. |
| 10,244,926 | B2 | 4/2019 | Noonan et al. |
| 10,285,574 | B2 | 5/2019 | Landey et al. |
| 10,299,870 | B2 | 5/2019 | Connolly et al. |
| 10,314,463 | B2 | 6/2019 | Agrawal et al. |
| 10,346,976 | B2 | 7/2019 | Averbuch |

(56) References Cited

U.S. PATENT DOCUMENTS

| | | |
|---|---|---|
| 10,383,765 B2 | 8/2019 | Alvarez et al. |
| 10,639,114 B2 | 5/2020 | Schuh |
| 10,667,875 B2 | 6/2020 | DeFonzo |
| 10,743,751 B2 | 8/2020 | Landey et al. |
| 10,751,140 B2 | 8/2020 | Wallace et al. |
| 10,765,487 B2 | 9/2020 | Ho |
| 10,820,954 B2 | 11/2020 | Marsot et al. |
| 2002/0077533 A1 | 6/2002 | Bieger et al. |
| 2002/0082612 A1* | 6/2002 | Moll .................. G09B 23/285 606/130 |
| 2002/0120188 A1 | 8/2002 | Brock et al. |
| 2002/0161280 A1 | 10/2002 | Chatenever et al. |
| 2002/0173878 A1 | 11/2002 | Watanabe |
| 2004/0047044 A1 | 3/2004 | Dalton |
| 2004/0263535 A1 | 12/2004 | Birkenbach et al. |
| 2005/0043718 A1* | 2/2005 | Madhani .................. A61B 34/77 606/1 |
| 2005/0085714 A1 | 4/2005 | Foley et al. |
| 2005/0193451 A1 | 9/2005 | Quistgaard et al. |
| 2005/0222554 A1 | 10/2005 | Wallace et al. |
| 2006/0079745 A1 | 4/2006 | Viswanathan |
| 2006/0095022 A1 | 5/2006 | Moll et al. |
| 2006/0142657 A1* | 6/2006 | Quaid .................. A61B 17/1764 600/424 |
| 2006/0173290 A1 | 8/2006 | Lavallee et al. |
| 2006/0200026 A1 | 9/2006 | Wallace et al. |
| 2007/0083098 A1 | 4/2007 | Stern et al. |
| 2007/0138992 A1 | 6/2007 | Prisco et al. |
| 2007/0144298 A1 | 6/2007 | Miller |
| 2007/0185486 A1 | 8/2007 | Hauck et al. |
| 2008/0027313 A1 | 1/2008 | Shachar |
| 2008/0033442 A1 | 2/2008 | Amoit |
| 2008/0082109 A1 | 4/2008 | Moll et al. |
| 2008/0097465 A1 | 4/2008 | Rollins et al. |
| 2008/0108870 A1 | 5/2008 | Wiita et al. |
| 2008/0140087 A1 | 6/2008 | Barbagli et al. |
| 2008/0159653 A1 | 7/2008 | Dunki-Jacobs et al. |
| 2008/0183068 A1 | 7/2008 | Caris et al. |
| 2008/0183188 A1 | 7/2008 | Carls et al. |
| 2008/0262372 A1 | 10/2008 | Manto et al. |
| 2008/0306490 A1 | 12/2008 | Lakin et al. |
| 2009/0248036 A1 | 10/2009 | Hoffman et al. |
| 2009/0259230 A1 | 10/2009 | Khadem |
| 2009/0259412 A1 | 10/2009 | Brogardh |
| 2009/0326556 A1 | 12/2009 | Diolaiti et al. |
| 2010/0019890 A1 | 1/2010 | Helmer et al. |
| 2010/0039506 A1 | 2/2010 | Sarvestani et al. |
| 2010/0076263 A1 | 3/2010 | Tanaka |
| 2010/0121269 A1 | 5/2010 | Goldenberg |
| 2010/0125284 A1 | 5/2010 | Tanner et al. |
| 2010/0161129 A1 | 6/2010 | Costa et al. |
| 2010/0204613 A1 | 8/2010 | Rollins et al. |
| 2010/0225209 A1 | 9/2010 | Goldberg |
| 2010/0328455 A1 | 12/2010 | Nam et al. |
| 2011/0021926 A1 | 1/2011 | Spencer |
| 2011/0113852 A1 | 5/2011 | Prisco |
| 2011/0118748 A1 | 5/2011 | Itkowitz |
| 2011/0118752 A1 | 5/2011 | Itkowitz et al. |
| 2011/0118753 A1 | 5/2011 | Itkowitz et al. |
| 2011/0130718 A1 | 6/2011 | Kidd et al. |
| 2011/0196199 A1 | 8/2011 | Donhowe et al. |
| 2011/0235855 A1 | 9/2011 | Smith |
| 2011/0238010 A1 | 9/2011 | Kirschenman et al. |
| 2011/0248987 A1 | 10/2011 | Mitchell |
| 2011/0276058 A1 | 11/2011 | Choi et al. |
| 2011/0306873 A1 | 12/2011 | Shenai et al. |
| 2012/0059392 A1 | 3/2012 | Diolaiti |
| 2012/0067354 A1 | 3/2012 | Lammertse |
| 2012/0071752 A1 | 3/2012 | Sewell |
| 2012/0071891 A1 | 3/2012 | Itkowitz et al. |
| 2012/0071892 A1 | 3/2012 | Itkowitz et al. |
| 2012/0071894 A1 | 3/2012 | Tanner et al. |
| 2012/0075638 A1 | 3/2012 | Rollins et al. |
| 2012/0078053 A1 | 3/2012 | Phee et al. |
| 2012/0103123 A1 | 5/2012 | McInroy et al. |
| 2012/0158011 A1 | 6/2012 | Sandhu |
| 2012/0203067 A1 | 8/2012 | Higgins et al. |
| 2012/0253276 A1 | 10/2012 | Govari et al. |
| 2012/0296161 A1 | 11/2012 | Wallace et al. |
| 2012/0314022 A1 | 12/2012 | Jo |
| 2013/0018306 A1 | 1/2013 | Ludwin |
| 2013/0060146 A1 | 3/2013 | Yang et al. |
| 2013/0165854 A1 | 6/2013 | Sandhu et al. |
| 2013/0245375 A1 | 9/2013 | DiMaio et al. |
| 2013/0317519 A1 | 11/2013 | Romo et al. |
| 2014/0107666 A1 | 4/2014 | Madhani |
| 2014/0111457 A1 | 4/2014 | Briden et al. |
| 2014/0142591 A1 | 5/2014 | Alvarez et al. |
| 2014/0171965 A1 | 6/2014 | Loh et al. |
| 2014/0222204 A1* | 8/2014 | Kawashima ............ B25J 13/02 700/258 |
| 2014/0276392 A1 | 9/2014 | Wong et al. |
| 2014/0276938 A1 | 9/2014 | Hsu et al. |
| 2014/0277333 A1 | 9/2014 | Lewis et al. |
| 2014/0357984 A1 | 12/2014 | Wallace et al. |
| 2014/0364870 A1 | 12/2014 | Alvarez et al. |
| 2015/0018622 A1 | 1/2015 | Tesar et al. |
| 2015/0051592 A1 | 2/2015 | Kintz |
| 2015/0105747 A1 | 4/2015 | Rollins et al. |
| 2015/0157191 A1 | 6/2015 | Phee et al. |
| 2015/0164594 A1 | 6/2015 | Romo et al. |
| 2015/0164596 A1 | 6/2015 | Romo |
| 2015/0224845 A1 | 8/2015 | Anderson et al. |
| 2015/0265807 A1 | 9/2015 | Park et al. |
| 2015/0290454 A1 | 10/2015 | Tyler et al. |
| 2015/0356878 A1 | 12/2015 | Warmerdam |
| 2015/0375399 A1 | 12/2015 | Chiu et al. |
| 2016/0001038 A1 | 1/2016 | Romo et al. |
| 2016/0026253 A1 | 1/2016 | Bradski et al. |
| 2016/0030268 A1 | 2/2016 | Meuleman |
| 2016/0059412 A1 | 3/2016 | Oleynik |
| 2016/0074123 A1 | 3/2016 | Bly et al. |
| 2016/0098095 A1 | 4/2016 | Gonzalez-Banos et al. |
| 2016/0183841 A1 | 6/2016 | Duindam et al. |
| 2016/0213436 A1 | 7/2016 | Inoue |
| 2016/0213884 A1 | 7/2016 | Park |
| 2016/0235496 A1 | 8/2016 | Hoffman et al. |
| 2016/0242858 A1 | 8/2016 | Moctezuma de la Barrera et al. |
| 2016/0256069 A1 | 9/2016 | Jenkins |
| 2016/0270865 A1 | 9/2016 | Landey et al. |
| 2016/0287279 A1 | 10/2016 | Bovay et al. |
| 2016/0314710 A1 | 10/2016 | Jarc |
| 2016/0314716 A1 | 10/2016 | Grubbs |
| 2016/0314717 A1 | 10/2016 | Grubbs |
| 2016/0324580 A1 | 11/2016 | Esterberg et al. |
| 2016/0374770 A1 | 12/2016 | Janik et al. |
| 2016/0375588 A1 | 12/2016 | Ueberle et al. |
| 2017/0007337 A1 | 1/2017 | Dan |
| 2017/0100199 A1 | 4/2017 | Yu et al. |
| 2017/0106537 A1 | 4/2017 | CHizeck et al. |
| 2017/0113019 A1 | 4/2017 | Wong et al. |
| 2017/0119481 A1 | 5/2017 | Romo et al. |
| 2017/0143429 A1 | 5/2017 | Richmond et al. |
| 2017/0165011 A1 | 6/2017 | Bovay et al. |
| 2017/0172664 A1 | 6/2017 | Weingarten et al. |
| 2017/0172673 A1 | 6/2017 | Yu et al. |
| 2017/0181808 A1 | 6/2017 | Panescu et al. |
| 2017/0189126 A1 | 7/2017 | Weir |
| 2017/0202627 A1 | 7/2017 | Sramek et al. |
| 2017/0209073 A1 | 7/2017 | Sramek et al. |
| 2017/0278427 A1 | 9/2017 | Karssen et al. |
| 2017/0278428 A1 | 9/2017 | Jonker et al. |
| 2017/0278432 A1 | 9/2017 | Lammertse et al. |
| 2017/0290631 A1 | 10/2017 | Lee et al. |
| 2017/0312481 A1 | 11/2017 | Covington et al. |
| 2017/0326737 A1 | 11/2017 | Martin et al. |
| 2017/0333139 A1 | 11/2017 | Suresh et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0014891 A1 | 1/2018 | Krebs et al. |
| 2018/0025666 A1 | 1/2018 | Ho et al. |
| 2018/0078320 A1 | 3/2018 | Griffiths |
| 2018/0078321 A1 | 3/2018 | Liao |

(56) References Cited

U.S. PATENT DOCUMENTS

| | | |
|---|---|---|
| 2018/0079090 A1* | 3/2018 | Koenig .................. A61B 34/37 |
| 2018/0147720 A1 | 5/2018 | Kell et al. |
| 2018/0177556 A1 | 6/2018 | Noonan et al. |
| 2018/0186005 A1 | 7/2018 | Hares |
| 2018/0193999 A1 | 7/2018 | Jacobsen et al. |
| 2018/0206927 A1 | 7/2018 | Prisco et al. |
| 2018/0214011 A1 | 8/2018 | Graetzel et al. |
| 2018/0214014 A1 | 8/2018 | Diolaiti |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271606 A1 | 9/2018 | Verner et al. |
| 2018/0271616 A1 | 9/2018 | Schuh et al. |
| 2018/0279852 A1 | 10/2018 | Rafii-Tar et al. |
| 2018/0280660 A1 | 10/2018 | Landey et al. |
| 2018/0289431 A1 | 10/2018 | Draper et al. |
| 2018/0289437 A1 | 10/2018 | Kurihara et al. |
| 2018/0296287 A1 | 10/2018 | Richmond et al. |
| 2018/0325499 A1 | 11/2018 | Landey et al. |
| 2018/0333044 A1 | 11/2018 | Jenkins |
| 2018/0360435 A1 | 12/2018 | Romo |
| 2018/0368930 A1 | 12/2018 | Esterberg et al. |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0090969 A1 | 3/2019 | Jarc et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0151032 A1 | 5/2019 | Mustufa et al. |
| 2019/0167361 A1 | 6/2019 | Walker et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0371012 A1 | 12/2019 | Flexman |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0345432 A1 | 11/2020 | Walker |
| 2020/0352420 A1 | 11/2020 | Graetzel |
| 2020/0360183 A1 | 11/2020 | Alvarez |
| 2020/0360659 A1 | 11/2020 | Wong |
| 2020/0367726 A1 | 11/2020 | Landey et al. |
| 2020/0367981 A1 | 11/2020 | Ho et al. |
| 2020/0375678 A1 | 12/2020 | Wallace |

FOREIGN PATENT DOCUMENTS

| | | |
|---|---|---|
| EP | 2 158 834 | 3/2010 |
| EP | 2 718 921 | 7/2016 |
| EP | 2 584 551 | 8/2017 |
| WO | WO 08/049088 | 4/2008 |
| WO | WO 10/025522 | 3/2010 |
| WO | WO 10/140016 | 12/2010 |
| WO | WO 16/026818 | 2/2016 |
| WO | WO 16/026819 | 2/2016 |
| WO | WO 16/026821 | 2/2016 |
| WO | WO-2017214243 A1 * | 12/2017 ............. A61B 34/37 |

* cited by examiner

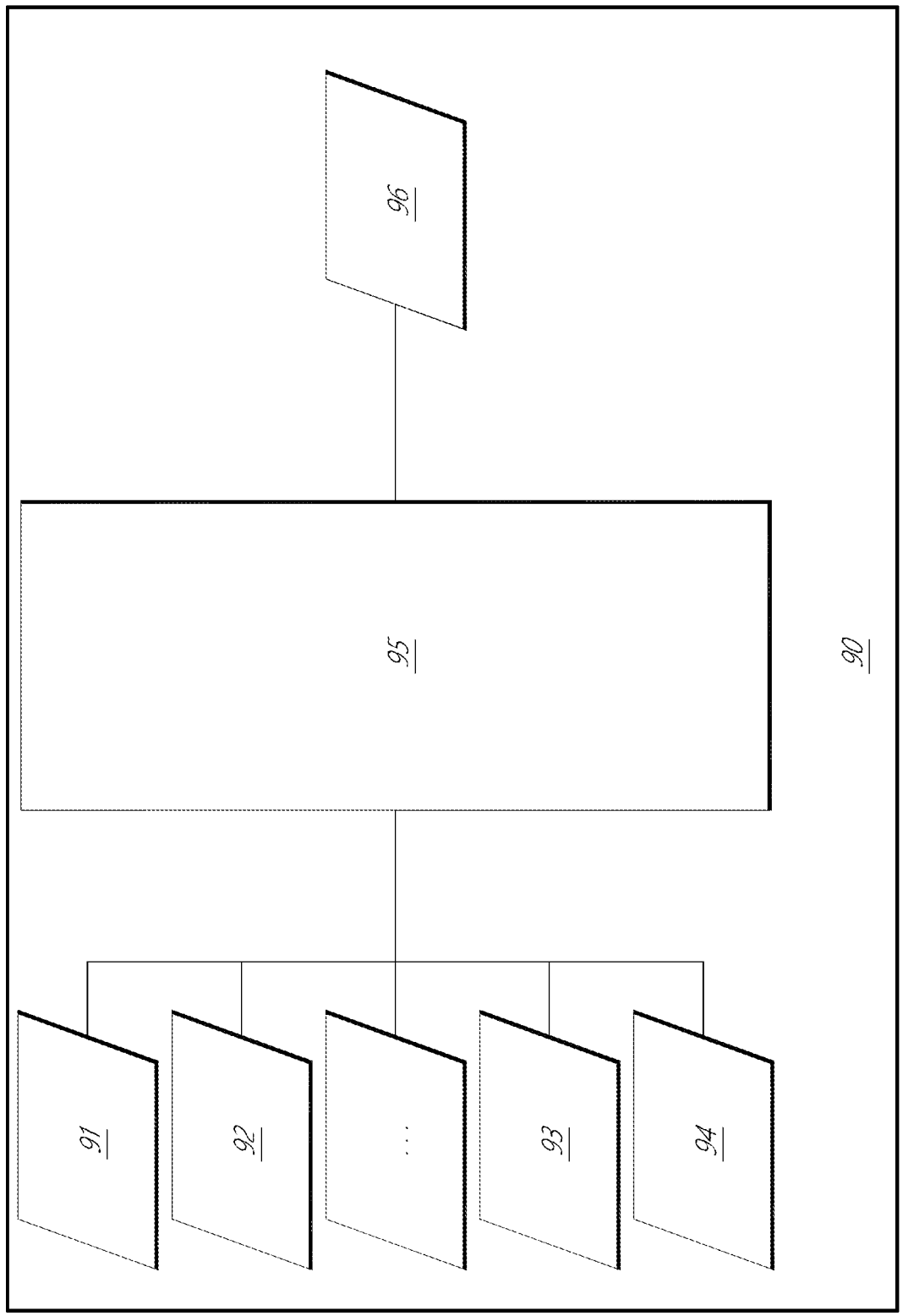

CONTROLLERS FOR ROBOTICALLY-ENABLED TELEOPERATED SYSTEMS

PRIORITY APPLICATION(S)

This application claims priority to U.S. Provisional Application No. 62/673,531, filed May 18, 2018, which is incorporated herein by reference. Any and all applications for which a foreign or domestic priority claim is identified in the Application Data Sheet as filed with the present application are hereby incorporated by reference under 37 CFR 1.57.

TECHNICAL FIELD

This application relates to controllers, and in particular, to controllers for robotically-enabled teleoperated systems including medical systems.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically-enabled medical system may be used to control the insertion and/or manipulation of the instrument and an end effector thereof. The robotically-enabled medical system may include a robotic arm, or other instrument positioning device. The robotically-enabled medical system may also include a controller used to control the positioning of the instrument during the procedure.

SUMMARY

In a first aspect, a robotically-enabled teleoperated system is described. The system includes a controller and a robotic tool capable of manipulation by the controller. The controller includes a handle configured for actuation by an operator; a gimbal coupled to the handle and configured to allow manipulation of the handle in multiple degrees of freedom, wherein the gimbal is configured for impedance control such that manipulation of the handle causes a corresponding manipulation of the robotic tool; and a positioning platform coupled to the gimbal and configured to allow manipulation of the handle in multiple degrees of freedom. The positioning platform is configured for admittance control such that manipulation of the handle causes a corresponding manipulation of the robotic tool.

The system may include one or more of the following features, in any combination: (a) wherein the robotic tool is a medical instrument; (b) wherein the gimbal is coupled to the positioning platform via a rotational joint; (c) wherein the gimbal allows manipulation of the handle in at least three rotational degrees of freedom; (d) wherein the positioning platform allows manipulation of the handle in at least three positional degrees of freedom; (e) a robotic arm coupled to the robotic tool, and wherein the robotic tool comprises at least one of a catheter, a scope, a grasper, a sealer, or a cutter; (f) a load cell positioned within the gimbal; (g) wherein the admittance control of the positioning platform is based on an output signal of the load cell; (h) wherein the gimbal comprises at least a first link, a second link, and a third link arranged distally to proximally and connected by joints, and wherein the load cell is positioned within the first link; (i) wherein the joints are revolute joints; (j) wherein the gimbal comprises at least a first joint, a second joint, and a third joint arranged distally to proximally and connected by links, and wherein the load cell is positioned distally of the second joint; (k) wherein the gimbal comprises at least a first link, a second link, and a third link arranged distally to proximally and connected by joints, and wherein the load cell is positioned within the third link; (l) the gimbal comprises at least a first joint, a second joint, and a third joint arranged distally to proximally and connected by links, and wherein the load cell is positioned proximally of the third joint; (m) wherein the gimbal comprises a cover attached to a distal end of the load cell that shields structure proximal to the load cell to thereby prevent a mechanical short between the distal end of the load cell and the shielded structure; (n) a motor positioned within the gimbal for controlling a joint of the gimbal; (o) wherein the motor is connected to the joint by a cable drive; (p) wherein the motor is located proximally of the joint; (q) wherein the positioning platform comprises at least one prismatic joint; (r) wherein an axis of motion of the prismatic joint is aligned with a direction of gravity; and/or (s) wherein the gimbal is coupled to the positioning platform by a joint, and wherein an axis of the joint is aligned with the direction of gravity.

In another aspect, a robotically-enabled teleoperated system includes a controller and a robotic tool capable of manipulation by the controller. The controller includes a handle configured for actuation by an operator; a gimbal coupled to the handle and configured to allow manipulation of the handle in multiple degrees of freedom, the gimbal comprising a load cell, wherein motion of at least two axes of the gimbal are not based on any output signal of the load cell; and a positioning platform coupled to the gimbal and configured to allow manipulation of the handle in multiple degrees of freedom. The handle is configured for admittance control based at least in part on an output signal of the load cell in the gimbal.

The system may include one or more of the following features, in any combination: (a) wherein the gimbal comprises at least a first link, a second link, and a third link arranged distally to proximally and connected by joints, and wherein the load cell is positioned within the first link; (b) a cover attached to a distal end of the load cell that shields structure proximal to the load cell thereby preventing a mechanical short between the distal end of the load cell and the shielded structure; (c) wherein the gimbal comprises at least a first joint, a second joint, and a third joint arranged distally to proximally and connected by links, and wherein the load cell is positioned distally of the second joint; (d) wherein the gimbal comprises at least a first link, a second link, and a third link arranged distally to proximally and connected by joints, and wherein the load cell is positioned within the third link; (e) wherein the gimbal comprises at least a first joint, a second joint, and a third joint arranged distally to proximally and connected by links, and wherein the load cell is positioned proximally of the third joint; (f) a motor positioned within the gimbal for controlling a joint of the gimbal; (g) wherein the motor is connected to the joint by a cable drive; and/or (h) wherein the motor is located proximally of the joint.

In another aspect, provided is a method for teleoperation that involves or includes: driving a controller's rotation via impedance control; driving a controller's translation via admittance control; delivering an output signal from the controller based on impedance and/or admittance control; and driving motion of the teleoperated tool based on the output signal.

The method may include one or more of the following features, in any combination: (a) wherein the output signal is based on the rotation and/or position of a handle of the controller; (b) wherein driving the controller's rotation via impedance control comprises rotating a handle of the controller; (c) wherein the handle is attached to a gimbal configured to allow manipulation of the handle in multiple degrees of freedom; (d) wherein the gimbal comprises a load cell; (e) wherein driving a controller's translation via admittance control comprises translating the handle of the controller, and wherein the admittance control is based on an output of the load cell; (f) wherein the gimbal comprises at least a first link, a second link, and a third link arranged distally to proximally and connected by joints, and wherein the load cell is positioned within the first link; (g) wherein the gimbal comprises at least a first joint, a second joint, and a third joint arranged distally to proximally and connected by links, and wherein the load cell is positioned distally of the second joint; (h) wherein the gimbal comprises at least a first link, a second link, and a third link arranged distally to proximally and connected by joints, and wherein the load cell is positioned within the third link; and/or (i) wherein the gimbal comprises at least a first joint, a second joint, and a third joint arranged distally to proximally and connected by links, and wherein the load cell is positioned proximally of the third joint.

In another aspect, provided is a method for teleoperation that includes: manipulating a controller to cause a corresponding manipulation of a teleoperated robotic tool, wherein manipulating the controller comprises: manipulating a handle of the controller in at least three rotational degrees of freedom through impedance control to cause corresponding manipulation of the teleoperated robotic tool; and manipulating the handle of the controller in at least three positional degrees of freedom through admittance control to cause corresponding manipulation of the teleoperated robotic tool.

The method may include one or more of the following features, in any combination: (a) wherein manipulating the handle in the at least three rotational degrees of freedom comprises manipulating a gimbal; (b) wherein manipulating the handle in the at least three rotational degrees of freedom comprises manipulating the handle in at least pitch, roll, and yaw; (c) wherein manipulating the handle in the at least three positional degrees of freedom comprises manipulating a positioning platform; and/or (d) wherein manipulating the handle in the at least three positional degrees of freedom comprises manipulating the handle in at least x-, y-, and z-directions.

In another aspect, a robotically-enabled teleoperated system includes a manipulator for manipulating a teleoperated robotic tool, the manipulator comprising a plurality of joints formed by links including a proximal most link and a distal most link operatively coupled to a column, wherein the proximal most link is positioned closer to the column than the distal most link. The system also includes a load cell positioned within at least one of the plurality of links. A first set of the plurality of joints is positioned proximal to the load cell and a second set of the plurality of joints is positioned distal to the load cell, and the second set of the plurality of joints includes at least one joint whose movement is not based on an output signal from the load cell.

The system may include one or more of the following features, in any combination: (a) wherein the manipulator comprises a serial link manipulator; (b) wherein the manipulator comprises a parallel link manipulator; (c) wherein the manipulator comprises a handle, a gimbal and a positioning platform formed by the plurality of links; (d) wherein the gimbal is coupled to the positioning platform by a revolute joint; (e) wherein the first set of the plurality of joints that are proximal to the load cell are part of a positioning platform; (f) wherein the manipulation of the positioning platform is based on an output of the load cell; and/or (g) wherein the second set of the plurality of joints that are distal to the load cell are part of a gimbal.

In another aspect, a robotically-enabled system includes a controller comprising a handle configured for actuation by an operator, a gimbal coupled to the handle and configured to allow manipulation of the handle in multiple degrees of freedom, wherein the gimbal is configured for impedance control, and a positioning platform coupled to the gimbal and configured to allow manipulation of the handle in multiple degrees of freedom, wherein the positioning platform is configured for admittance control. In some embodiments, the controller manipulates a teleoperated robotic tool. In some embodiments, the controller manipulates an object in a virtual environment.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 15 depicts a block diagram illustrating a localization system that estimates a location of one or more elements of the robotic systems of FIGS. 1-10, such as the location of the instrument of FIGS. 13 and 14, in accordance to an example embodiment.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
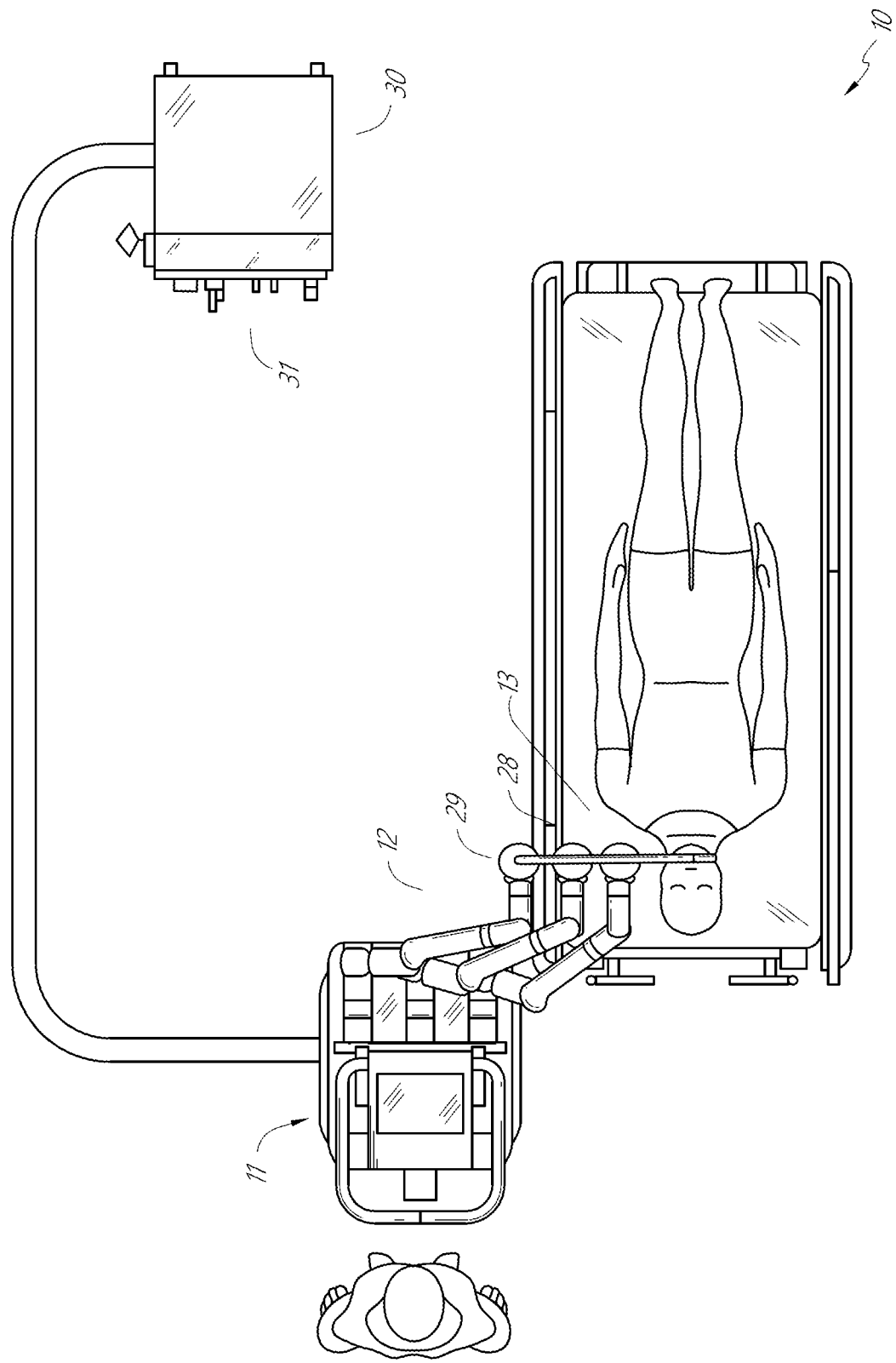
FIG. 1 illustrates an embodiment of a cart-based robotic system arranged for diagnostic and/or therapeutic bronchoscopy procedure(s).
Figure 2:
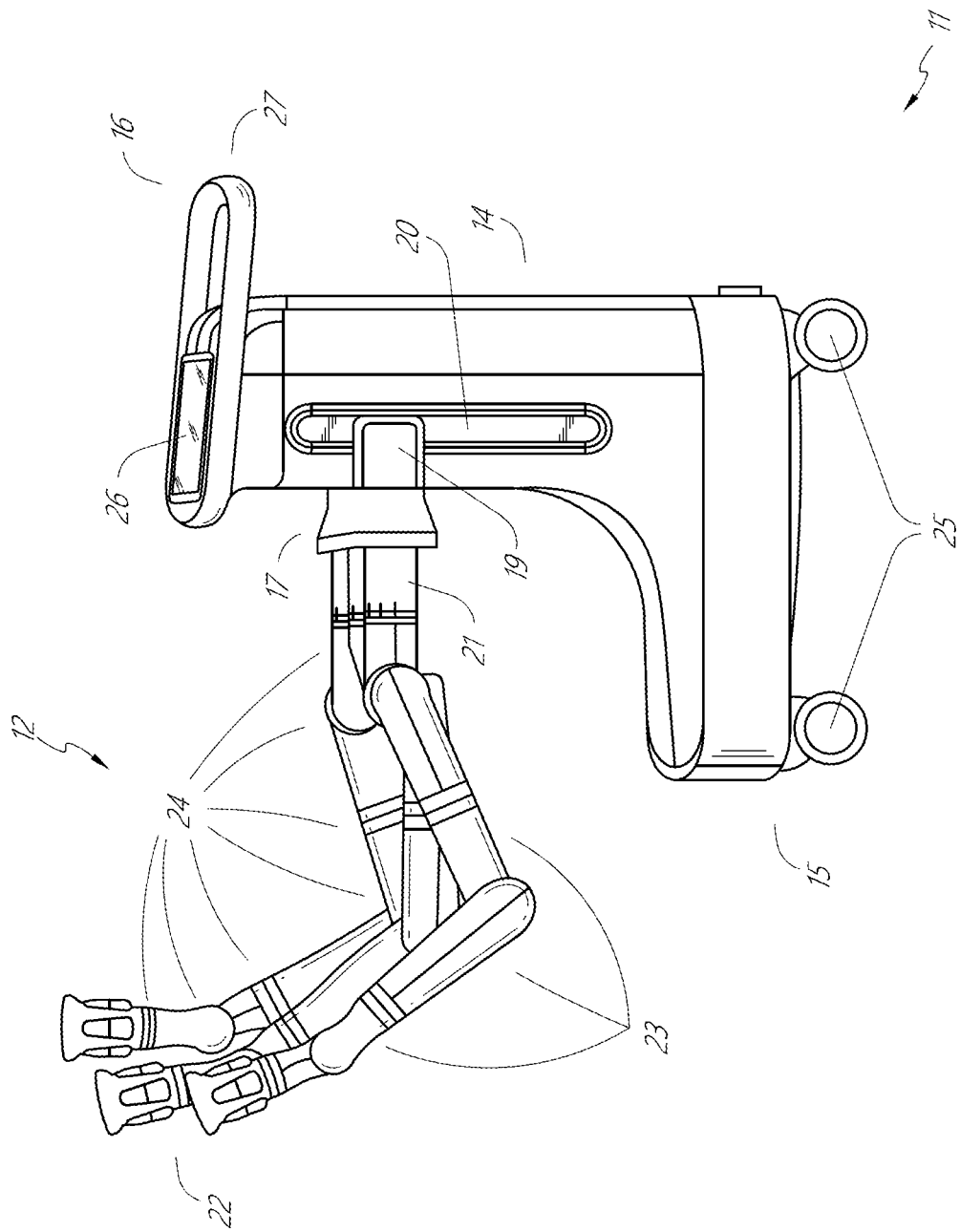
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 31 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
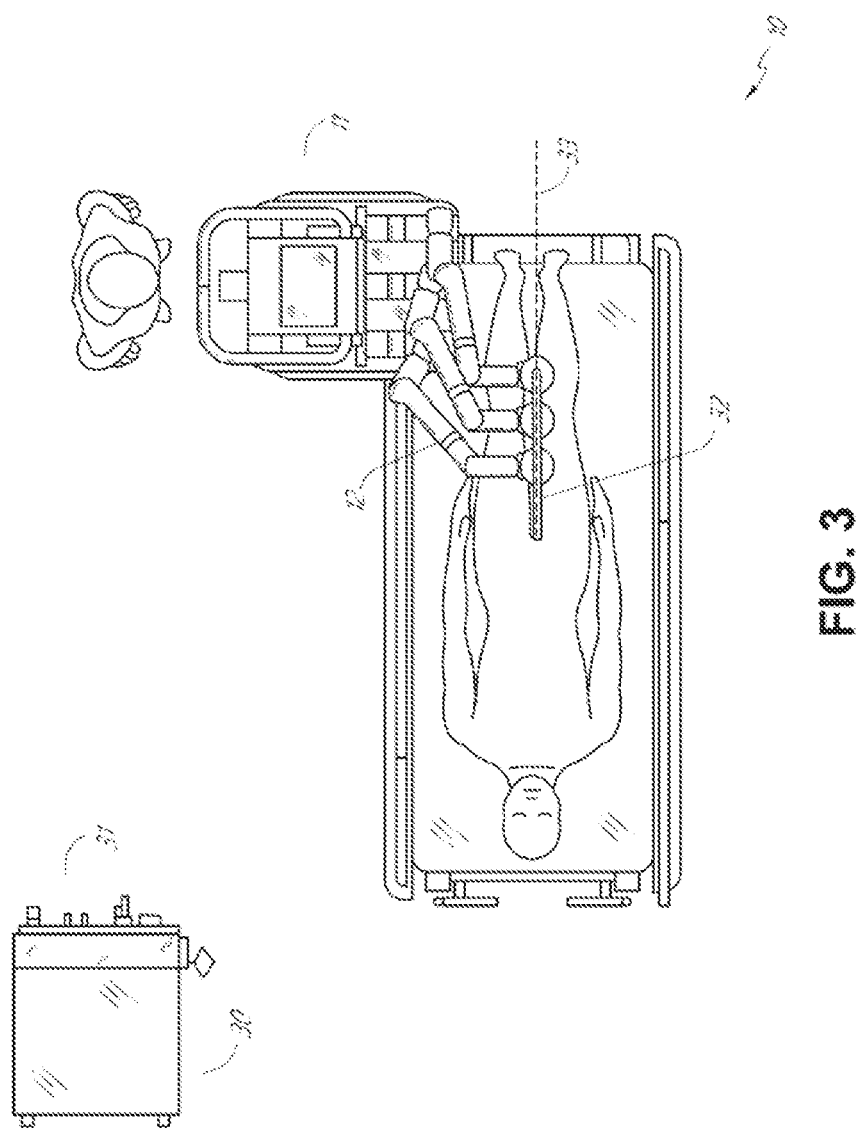
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
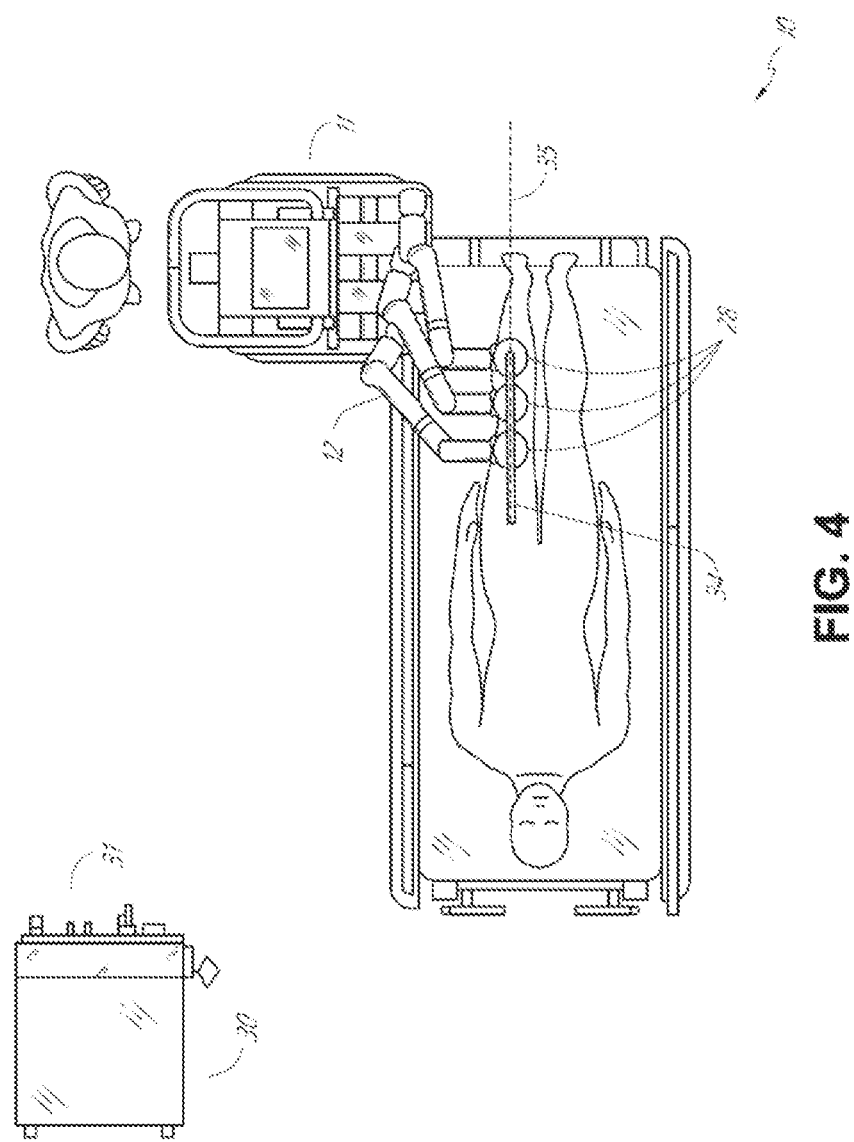
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
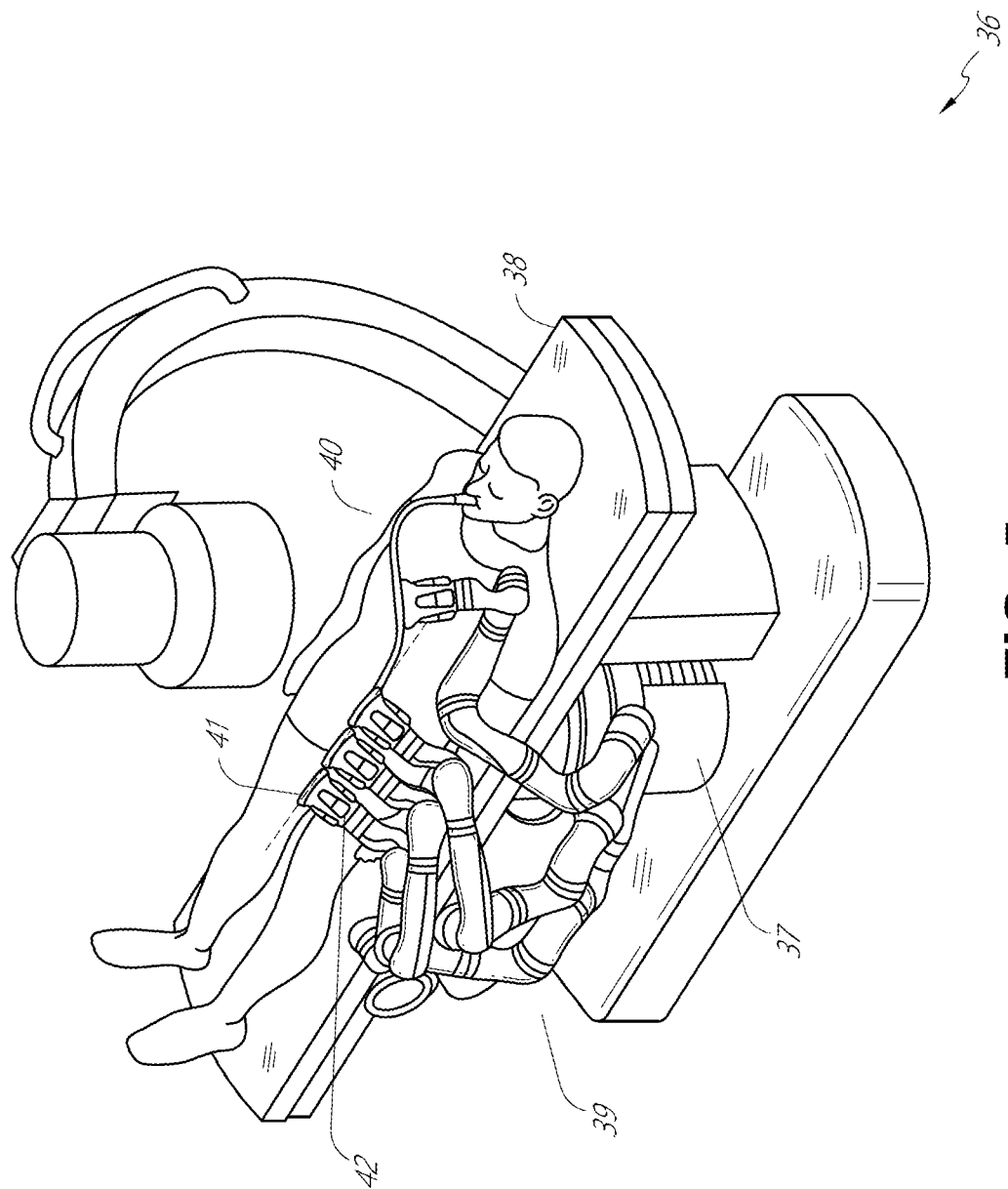
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
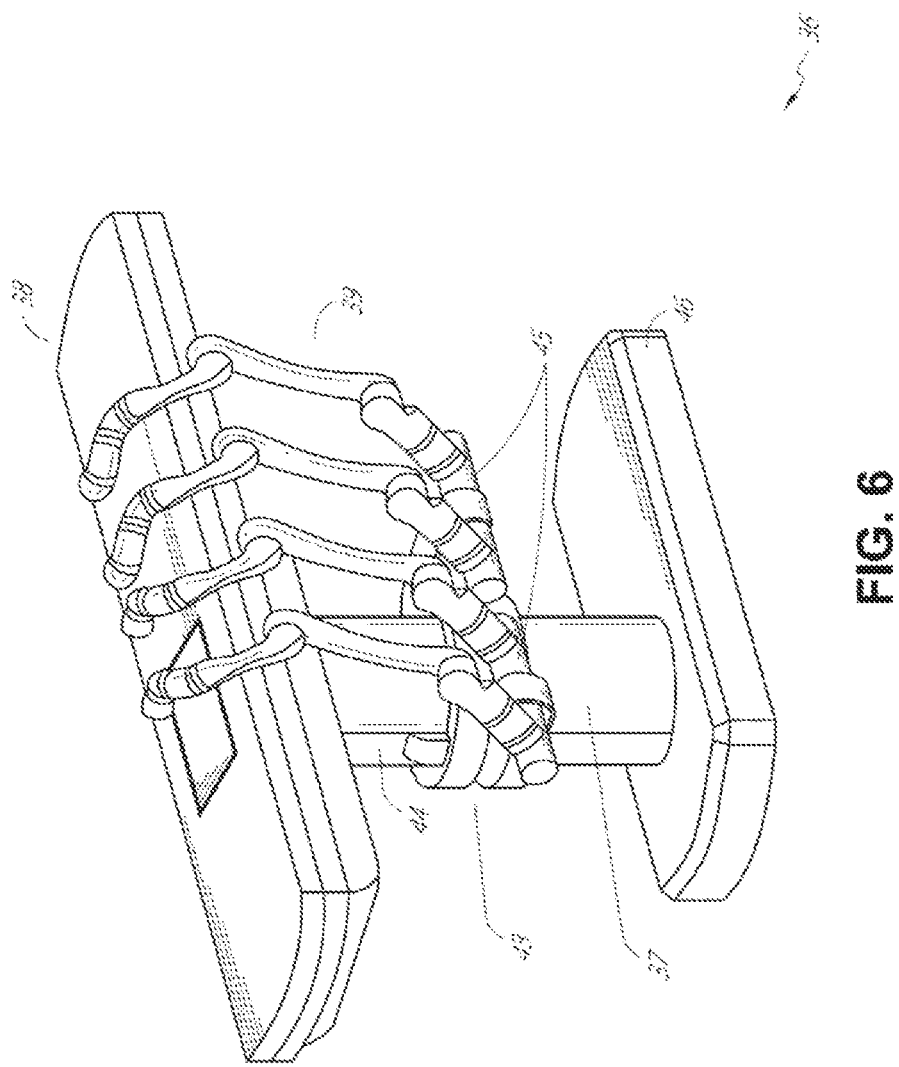
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
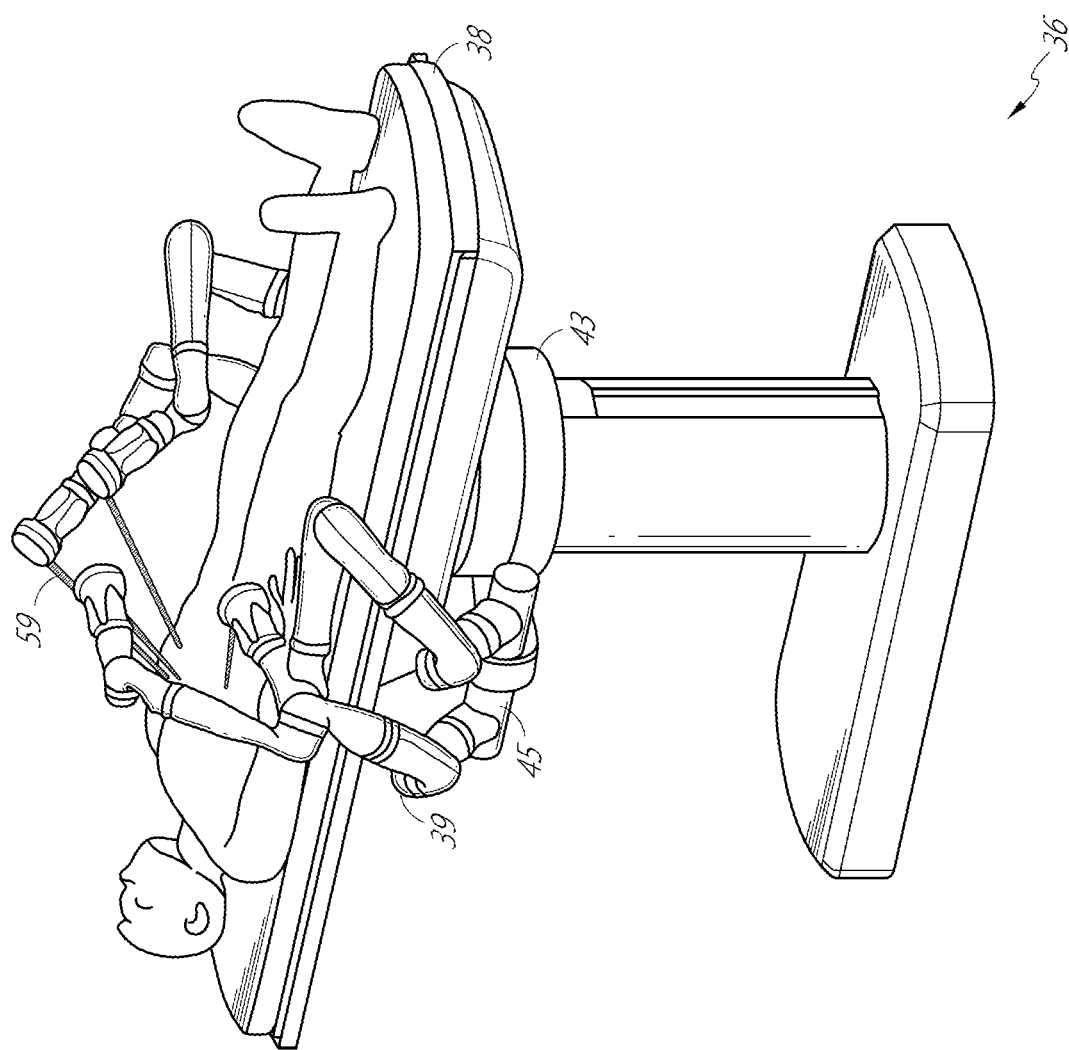
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
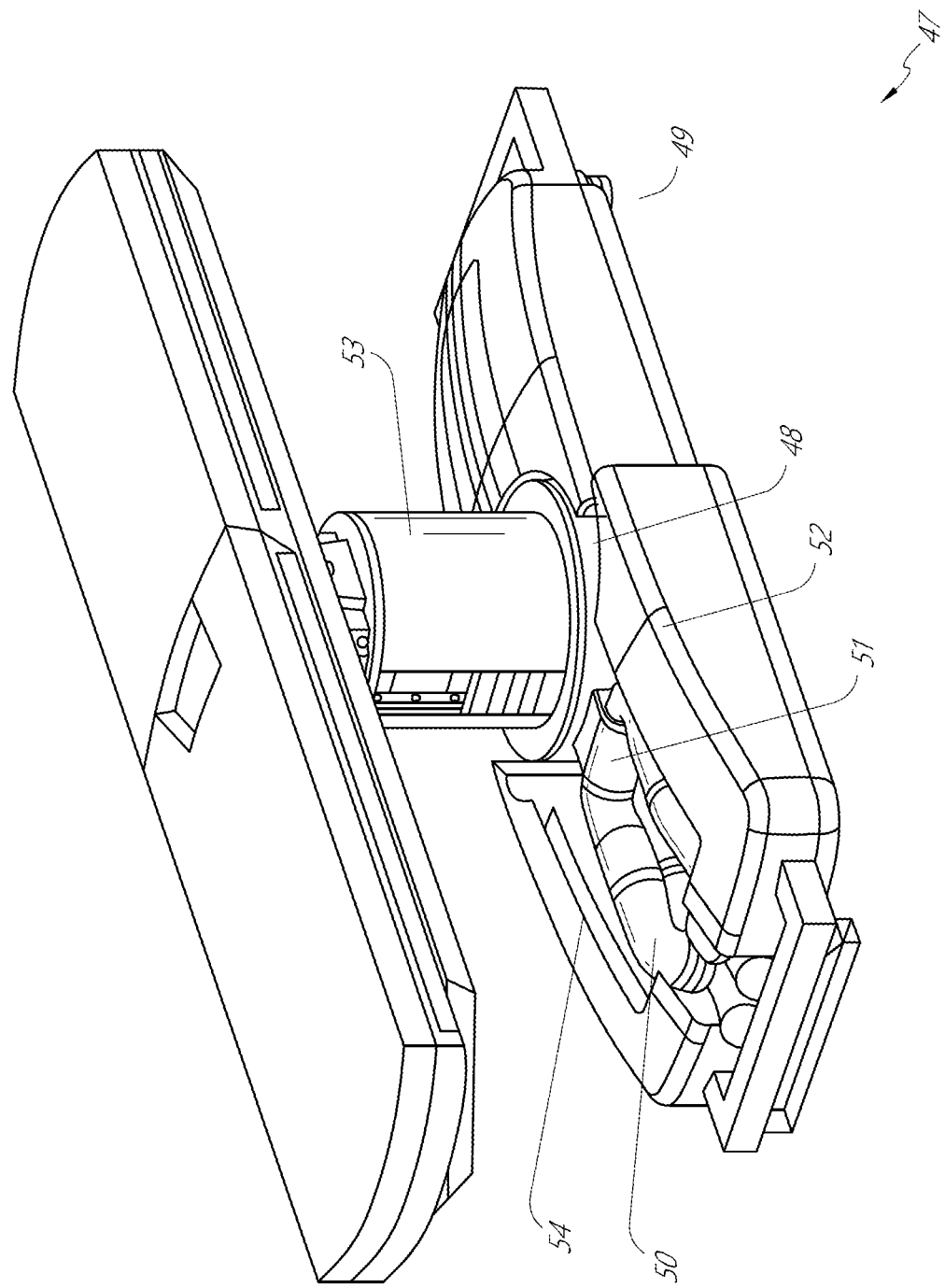
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
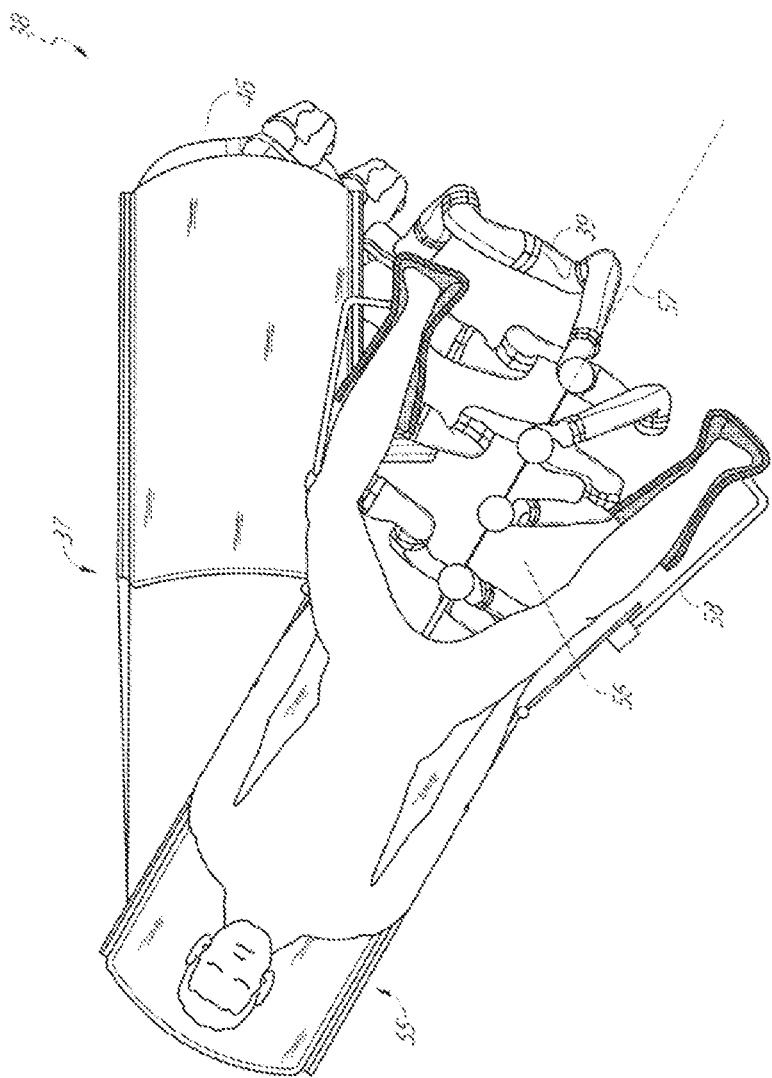
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
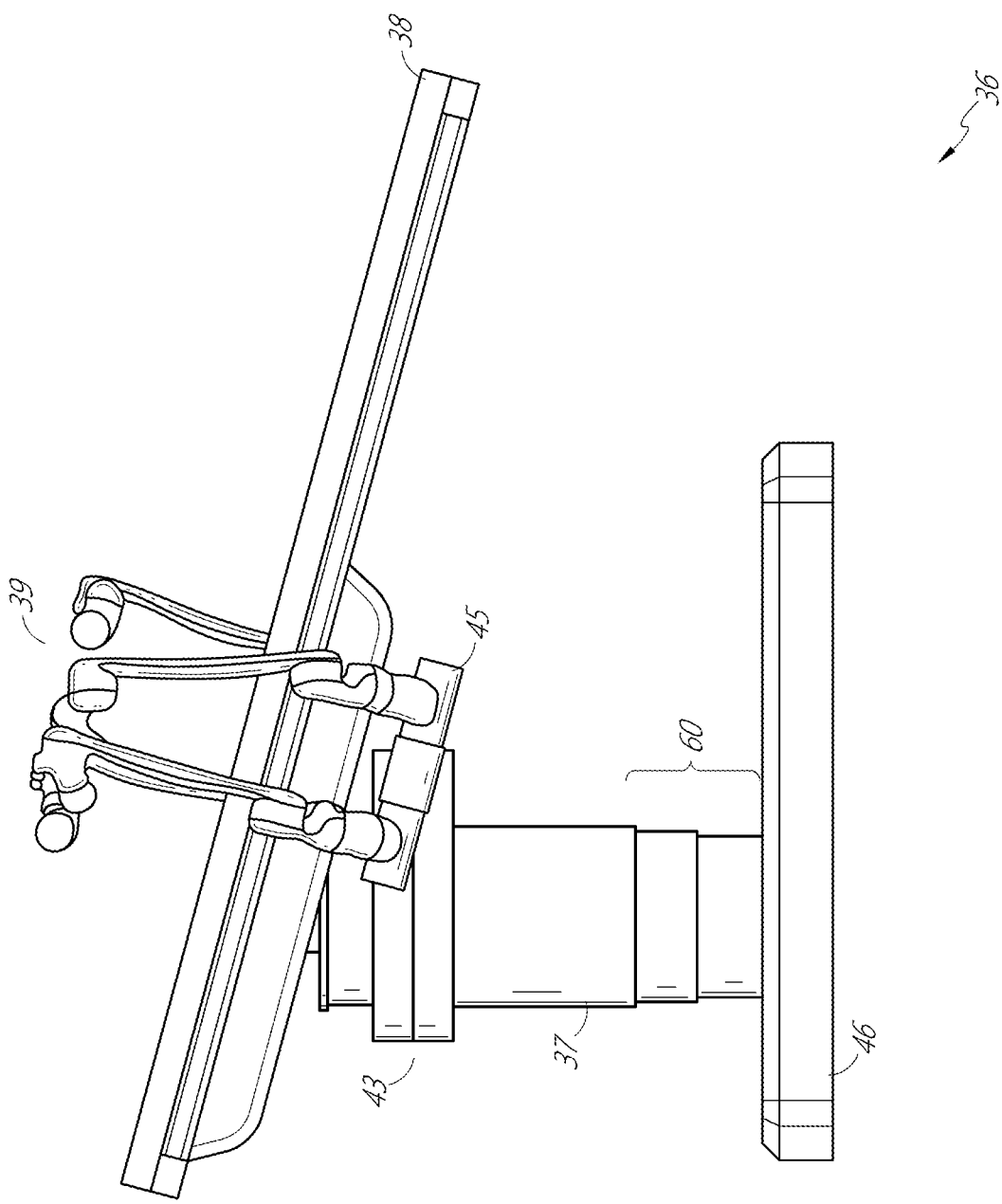
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
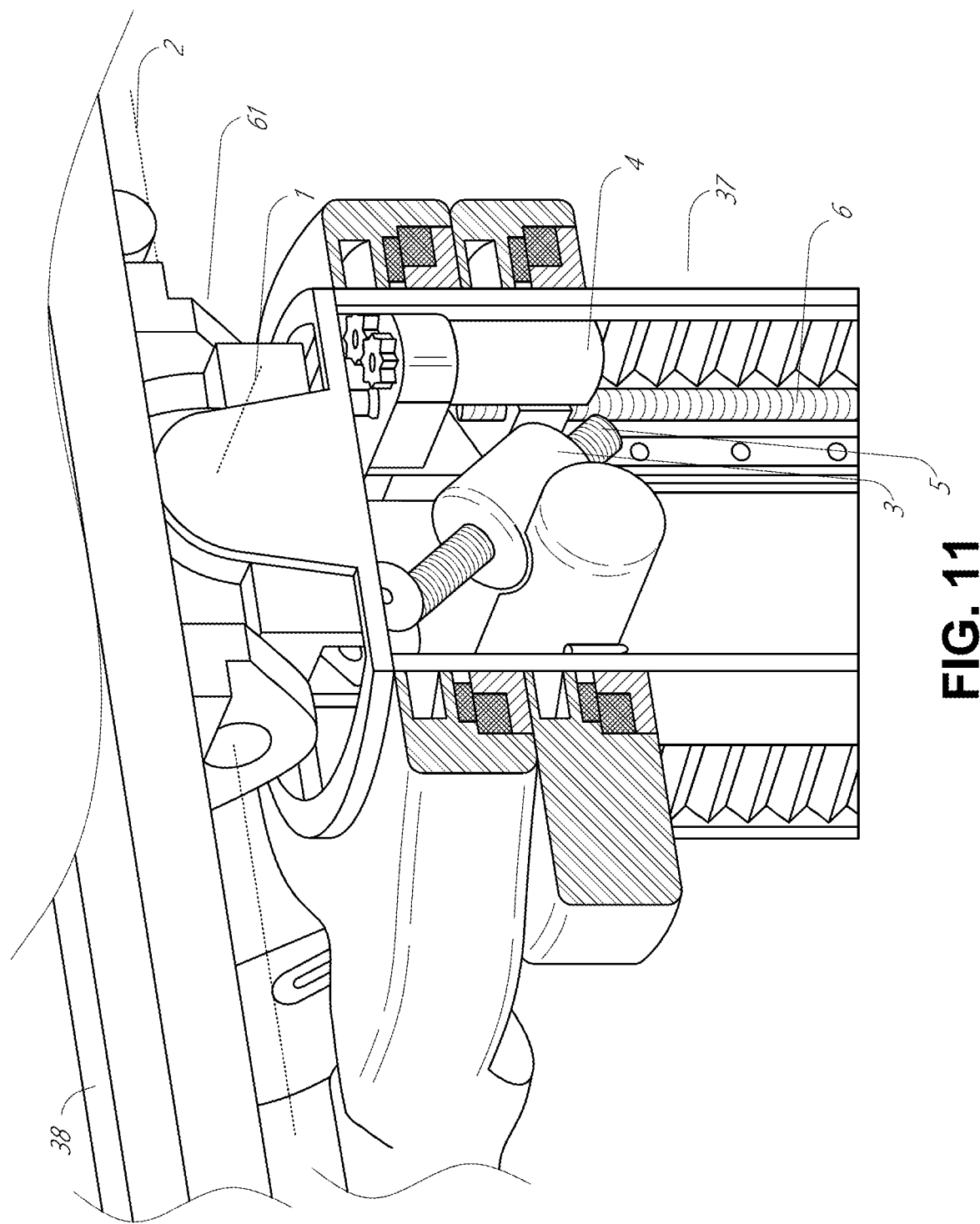
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper/higher abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
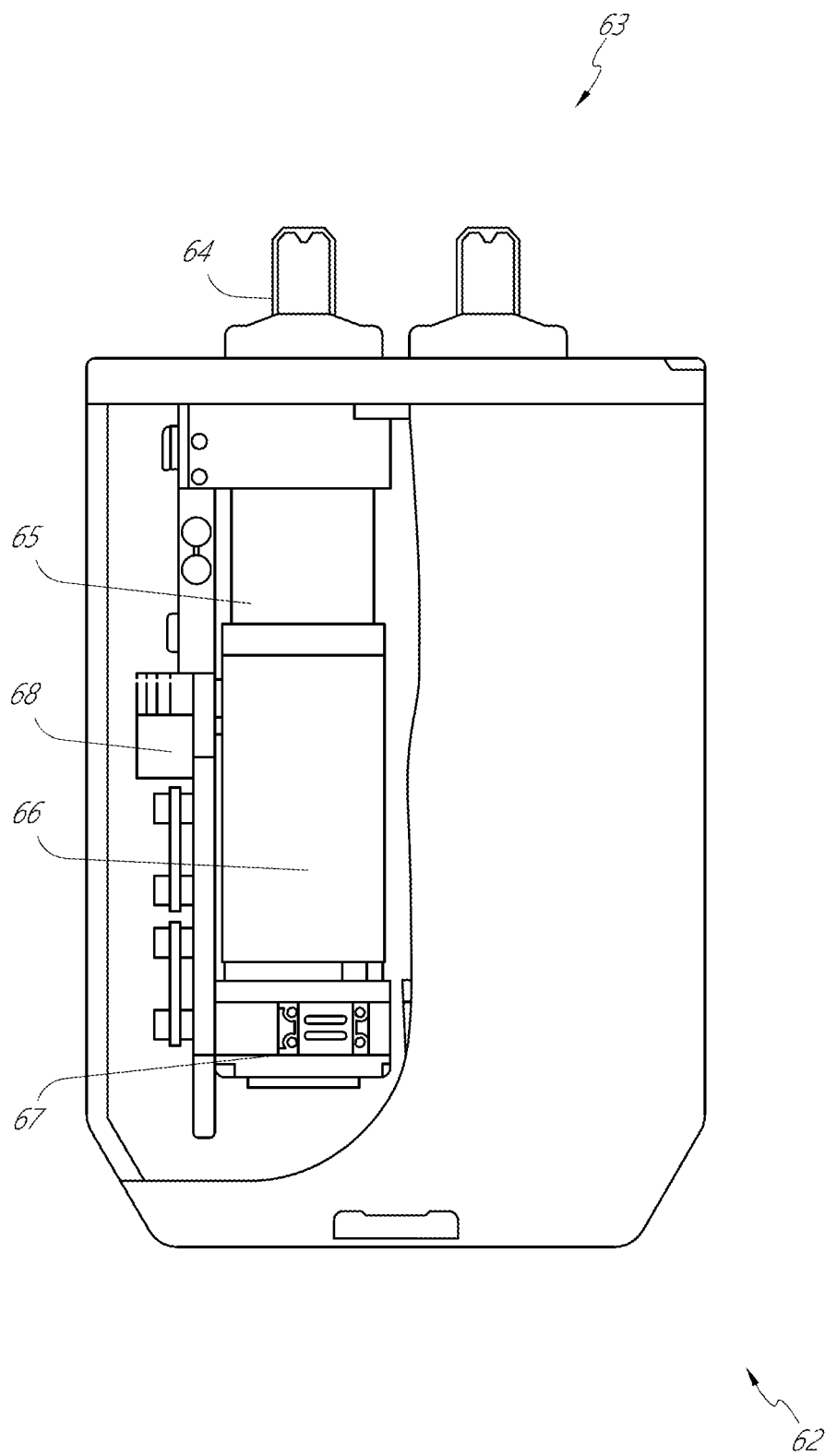
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
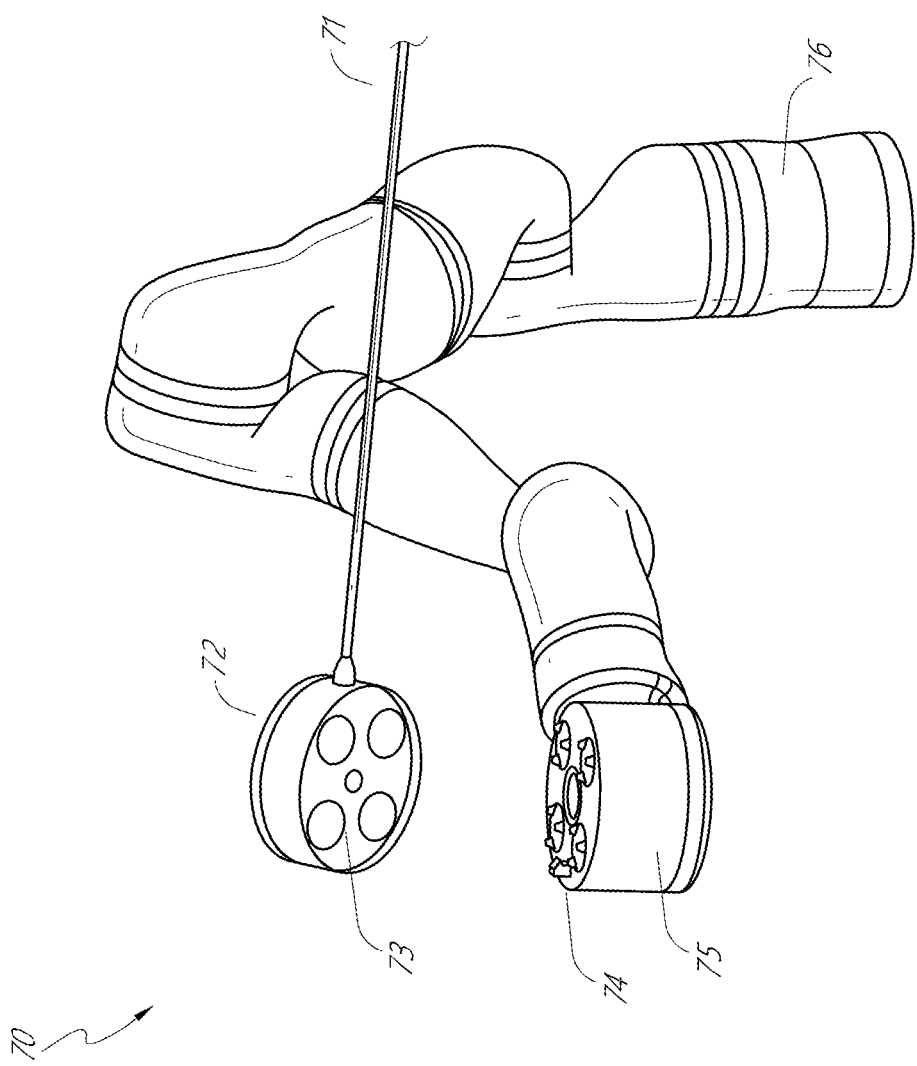
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 14:
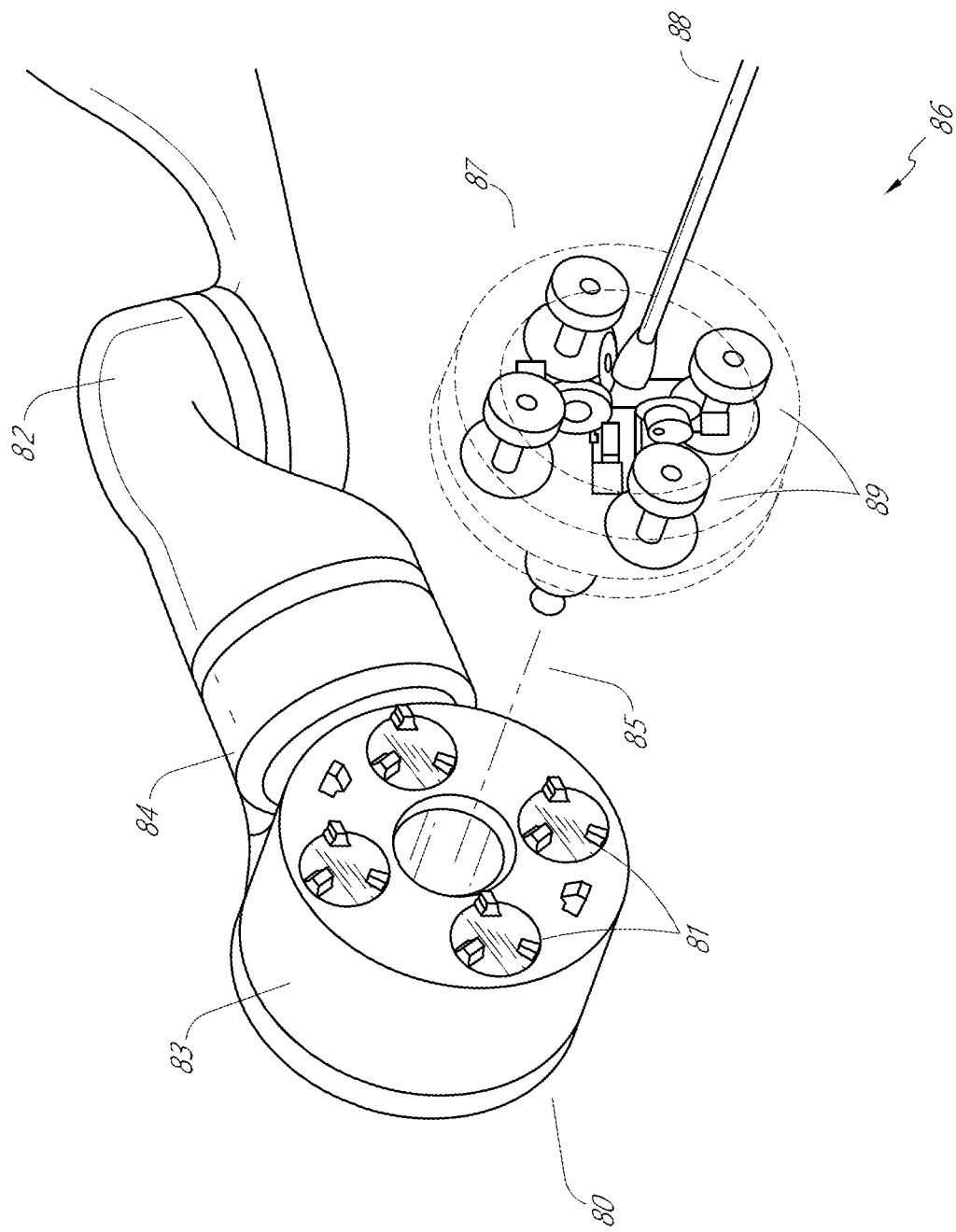
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Controllers for Robotically-Enabled Teleoperated Systems

Robotically-enabled teleoperated systems, such as the systems described above, can include an input device or controller that is configured to allow an operator (e.g., a physician performing a robotically-enabled medical procedure) to manipulate and control one or more instruments. In some embodiments, the robotically-enabled teleoperated systems comprise a controller for operating one or more medical tools. One skilled in the art will appreciate that the controllers described herein can be applied in non-medical contexts as well. For example, the controllers can be useful for manipulating tools that involve hazardous substances. In addition, in some embodiments, the controllers described herein can be useful in grabbing objects in physical and/or virtual environments. In some embodiments, the controllers can be self-sufficient as service robots interacting with human operators. In some embodiments, the controller can be coupled (e.g., communicatively, electronically, electrically, wirelessly, and/or mechanically) with an instrument (such as, e.g., a medical instrument) such that manipulation of the controller causes a corresponding manipulation of the instrument. In some embodiments, the controller and the instrument are arranged in a master-slave pair. In some embodiments, the controller may be referred to as a manipulator, emulator, master, interface, etc. In some embodiments, the controller can comprise a plurality of links assembled in parallel or in series.

The controller can serve as an input device for an operator to control the actions of a medical instrument, such as in an endoscopic, endoluminal, laparoscopic, or open surgery instrument. Movement of the controller by the operator can direct the movement of the medical instrument. For example, when an operator translates the controller in three-dimensional space (e.g., up, down, left, right, backwards, forwards), the system can cause a corresponding translation of the medical instrument. Similarly, if the operator rotates the controller (e.g., around any of three orthogonal axes) the system can cause a corresponding rotational movement of the medical instrument. The controller can also include an input that allows the operator to actuate the medical instrument. As one example, if the medical instrument includes a grasper, the controller can include an input that allows the operator to open and close the grasper.

The controller can also provide haptic feedback to the operator. For example, in some embodiments, forces or torques imparted on the medical instrument can be transmitted back to the operator through the controller. In some embodiments, providing haptic feedback to the operator through the controller provides the user with an improved operating, controlling, or driving experience. In some embodiments, to make it easier for the operator to interact with the controller and operate the system, crisp haptic cues can be provided.

In some embodiments, the controller is also used to align the operator's hands with the orientation of a medical instrument, for example, when switching medical instruments. For example, if a medical instrument is positioned within a patient during a medical procedure, it is important that the medical instrument does not move unexpectedly or unintentionally. Thus, when an operator desires to take control of a medical instrument already positioned within the body, the controller can first move to match the orientation of the medical instrument, while the instrument remains in place. With the controller correctly oriented to match the orientation of the medical instrument, the operator can then use the controller to manipulate the medical instrument.

In some embodiments, robotically-enabled medical systems include controllers with seven degrees of freedom that follow the operator's hand movement, with the seven degrees of freedom including three positional degrees of freedom (e.g., translational movement in x, y, z space), three rotational degrees of freedom (e.g., rotational movement around pitch, roll, and yaw axes), and one (or more) instrument actuation degree of freedom (e.g., an angular degree of freedom). In some embodiments, the instrument actuation degree of freedom can control the opening and closing of an end effector of the medical instrument, such as a gripper or grasper to hold an object. In some embodiments, the instrument actuation degree of freedom may be omitted. In some embodiments, controllers may include greater or fewer numbers of degrees of freedom. For example, in some embodiments, a controller may include more than three positional degrees of freedom or more than three rotational degrees of freedom to provide one or more redundant degrees of freedom. In some embodiments, redundant degrees of freedom may provide additional mechanical flexibility for the controller, for example, to avoid singularities caused by the mechanical structure of the controller.

Figure 16A:
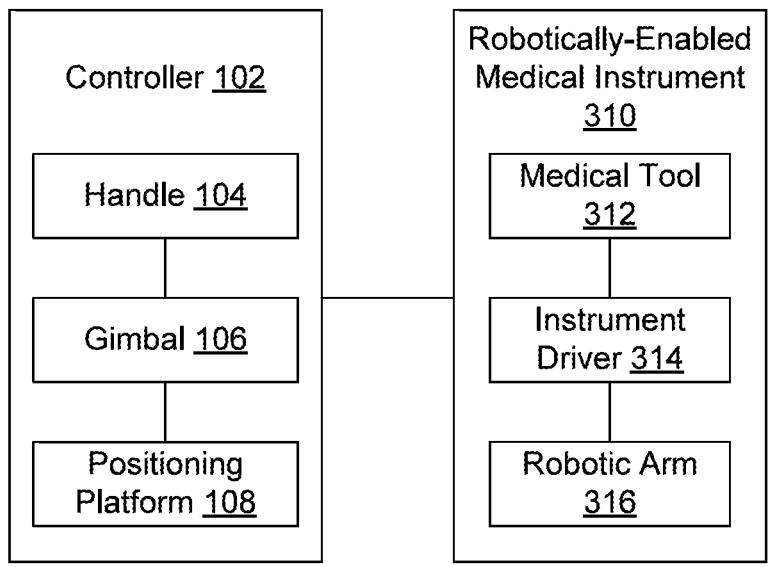
FIG. 16A is a block diagram illustrating an embodiment of a robotically-enabled medical system including a controller for a robotically-enabled medical instrument.

FIG. 16A illustrates a block diagram of an embodiment of a robotically-enabled medical system 100 including a schematic representation of an embodiment of a controller 102 and schematic representation of an embodiment of a robotically-enabled medical instrument 310. As briefly mentioned above, the controller 102 can be coupled with the robotically-enabled medical instrument 310 such that manipulation of the controller 102 causes a substantially corresponding movement of the robotically-enabled medical instrument 310, and forces imparted on the robotically-enabled medical instrument 310 can be transmitted back to the controller and haptically communicated to the operator. In some embodiments, the controller 102 and the robotically-enabled medical instrument 310 are arranged in a master-slave configuration.

In the illustrated embodiment of the system 100, the controller 102 includes a handle 104, a gimbal 106, and a positioning platform 108. The handle 104 can be configured to be held by the operator. As illustrated, in some embodiments, the handle 104 is coupled to the gimbal 106 and the positioning platform 108. As noted above, the handle 104 can include one or more degrees of freedom to actuate an instrument. The gimbal 106 can be configured to provide one or more rotational degrees of freedom to allow the operator to rotate the handle 104. In some embodiments, the gimbal 106 is configured to provide at least three rotational degrees of freedom. For example, the gimbal 106 can be configured to allow the operator to rotate the handle 104 about pitch, roll, and yaw axes. Example gimbals 106 are shown in FIGS. 17-19B and described in greater detail below. The positioning platform 108 can be configured to provide one or more translational (also referred to herein as positional) degrees of freedom to allow the operator to translate the handle 104. In some embodiments, the positioning platform 108 is configured to provide at least three positional degrees of freedom. For example, the positioning platform 108 can be configured to allow the operator to translate the handle 104 in three dimensional space (e.g., x-, y-, and z-directions). An example positioning platform 108 can be seen in FIG. 16C, described in greater detail below. Together, the gimbal 106 and the positioning platform 108 can enable the user to manipulate the handle 104.

In the illustrated embodiment, the robotically-enabled medical instrument 310 includes an instrument or tool 312 (which may include an end effector), an instrument driver 314, and a robotic arm 316 (or other instrument positioning device). The medical tool 312 can be, for example, the laparoscopic instrument 59 shown in FIG. 9 above, as well as other types of endoscopic or laparoscopic medical instruments as described throughout this application and as will be apparent to those of ordinary skill in the art. The medical tool 312 can include an end effector or a plurality of end effectors. The end effector can be positioned on a distal end of the medical tool 312. The end effector can be configured for insertion into the patient's body. In some embodiments, the end effector can be a grasper, a gripper, a cutter, a basketing apparatus, or a scissor, among many others. In some embodiments, the medical tool 312 can comprise a scope or a camera.

The medical tool 312 can be attached to the instrument driver 314. The instrument driver 314 can be configured to actuate the medical tool 312 as described above. For example, the instrument driver 314 can be configured to pull one or more pull wires of the medical tool 312 to actuate the medical tool 312. In some embodiments, the instrument driver 314 can be an instrument drive mechanism as described above. The instrument driver 314 can be attached to the robotic arm 316, for example, as shown in FIG. 13. The robotic arm 316 can be configured to articulate or move to further manipulate and position the medical tool 312. Example medical instruments/tools, instrument drivers, and robotic arms are shown in the systems of FIGS. 1-15, described above.

The controller 102 can be coupled to the robotically-enabled medical instrument 310 such that manipulation of the handle 104 causes substantially corresponding movement of the medical tool 312 and forces imparted on the medical tool 312 can be haptically transmitted to the operator through the handle 104. Manipulation of the handle 104 can be measured or determined by measuring forces and movements of the gimbal 106 and the positioning platform 108. Movement of the medical tool 312 can be caused by articulation and movement of the instrument driver 314 and/or the robotic arm 316. Thus, by manipulating the handle 104, the operator can control the medical tool 312.

In many instances, it is desired that the controller 102 be easily manipulated by the operator such that the operator has fine and precise control over the medical tool 312 and can use the controller 102 without becoming over-tired. One metric for measuring the ease of manipulation of a controller is the perceived inertia and/or perceived mass of the system. In some embodiments, the perceived inertia of the system is the mass of the system that the user feels as if it were a point mass when manipulating the handle 104. In general, controllers 102 with lower perceived inertia may be easier to operate. In other embodiments, the perceived inertia includes the moment of inertia that the user feels when manipulating the handle 104.

As will be described below, the controllers described in this application include several novel and nonobvious features which provide advantages over existing systems. In some embodiments, the controllers described herein are advantageously configured to operate with both admittance and impedance control. As described below, a hybrid controller including both admittance and impedance control, can provide an improved operating experience. In some embodiments, a hybrid controller including both admittance and impedance control can advantageously provide a lower or reduced perceived inertia when compared with other controllers. In some embodiments, a hybrid controller can provide improved haptic feedback and response. Further, as described below, in some embodiments, the controllers described herein can prevent or reduce the likelihood of mechanical shorts (described below), which can cause erratic and unpredictable movement. These and other features and advantages of the controllers described in this application are further discussed in the following sections.

A. Hybrid Controllers

Figure 16B:
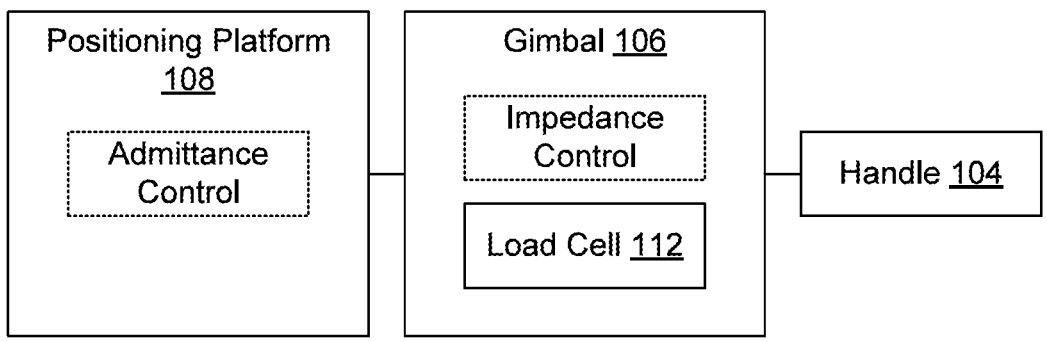
FIG. 16B is a block diagram illustrating an embodiment of the controller of FIG. 16A, which can be configured for hybrid impedance and admittance control.

FIG. 16B is a block diagram of an embodiment of a controller 102 configured to operate using both impedance and admittance control. Such a controller 102 can be referred to as a hybrid controller.

Impedance control and admittance control are two control schemes for controlling a robotic system. Under impedance control, the system measures displacements (e.g., changes in position and velocity) and outputs forces. For example, for impedance control, the system can measure how far or fast an operator moved the controller, and, based on the measurement, generate forces on the instrument (e.g., by actuating motors). Under impedance control, the operator's movement of the controller may back drive portions of the instrument. In many cases, the use of impedance control can result in a large perceived inertia. This can be because, for example, impedance control relies on the operator moving the controller. Under impedance control, the operator may have to overcome the perceived mass or inertia of the controller in order to move it, causing the controller to feel heavy. For impedance control, the operator must physically overcome most or all of the inertia in the system in order to move the controller. Other controllers have relied solely on impedance control, which can cause the systems to have higher perceived inertia or mass when compared to the controllers described herein. Because of the higher perceived inertia, operators can over-tire when using such other controllers.

Under admittance control, the system measures forces and/or torques imparted on the controller by the operator and outputs corresponding velocities and/or positions of the controller. In some respects, admittance control is the opposite of impedance control. In some embodiments, the use of admittance control can advantageously result in a decrease in the perceived inertia or mass of a system. Admittance control can be used to change the dynamics of a controller that is perceived as having a high mass or inertia. In some instances, by using admittance control, the operator need not overcome all of the inertia in the system to move the controller. For example, under admittance control, when a user imparts a force on the controller, the system can measure the force and assist the user in moving the controller by driving one or more motors associated with the controller, thereby resulting in desired velocities and/or positions of the controller. Stated another way, for admittance control, a force sensor or load cell measures the force that the operator is applying to the controller and moves the controller as well as the coupled robotically-enabled medical instrument 310 in a way that feels light. Admittance control may feel lighter than impedance control because, under admittance control, one can hide the perceived inertia of the controller because motors in the controller can help to accelerate the mass. In contrast, with impedance control, the user is responsible for all or substantially all mass acceleration.

As shown in the illustrated embodiment in FIG. 16B, the controller 102 includes a handle 104, a gimbal 106, and a positioning platform 108. As described above, the gimbal 106 can be configured to provide one or more rotational degrees of freedom (e.g., three or four), and the positioning platform 108 can be configured to provide one or more rotational degrees of freedom (e.g., three or four). The gimbal 106 and the positioning platform 108 can allow the user to move the handle 104 in three dimensional space and rotate the handle 104 around pitch, roll, and yaw axes. Manipulation of the handle 104 results in movement of a corresponding medical instrument. Further, the handle 104, gimbal 106, and positioning platform 108 can be configured to provide haptic feedback to the operator representative of forces imparted on the medical instrument.

As illustrated by the dashed boxes in FIG. 16B, in the controller 102, the gimbal 106 is configured for impedance control and the positioning platform 108 is configured for admittance control. Accordingly, for some embodiments, the translational or positional degrees of freedom of the positioning platform 108 rely on admittance control, while the rotational degrees of freedom of the gimbal 106 rely on impedance control. As described further below, this type of hybrid controller 102 can have several advantages. In other embodiments (not shown), the gimbal 106 is configured for admittance control and the positioning platform 108 is configured for impedance control. In some embodiments, the gimbal 106 and the positioning platform can be both be configured for admittance control or both be configured for impedance control.

To utilize admittance control, the controller 102 includes at least one force sensor or load cell 112. The load cell 112 is configured to measure forces imparted on the controller 102 (generally, forces imparted on the handle 104) by the operator. The output signal of the load cell 112 (a measure of force) is used to provide control signals that control movement of the controller 102, such as the positioning platform 108. The robotically-enabled medical instrument 310 will follow the motion of the handle 104 (e.g., by activating one or more motors in the instrument driver 314 or the robotic arm 316). In some embodiments, the load cell 112 can be a three degree of freedom load cell, which measures forces in three directions.

Figure 18:
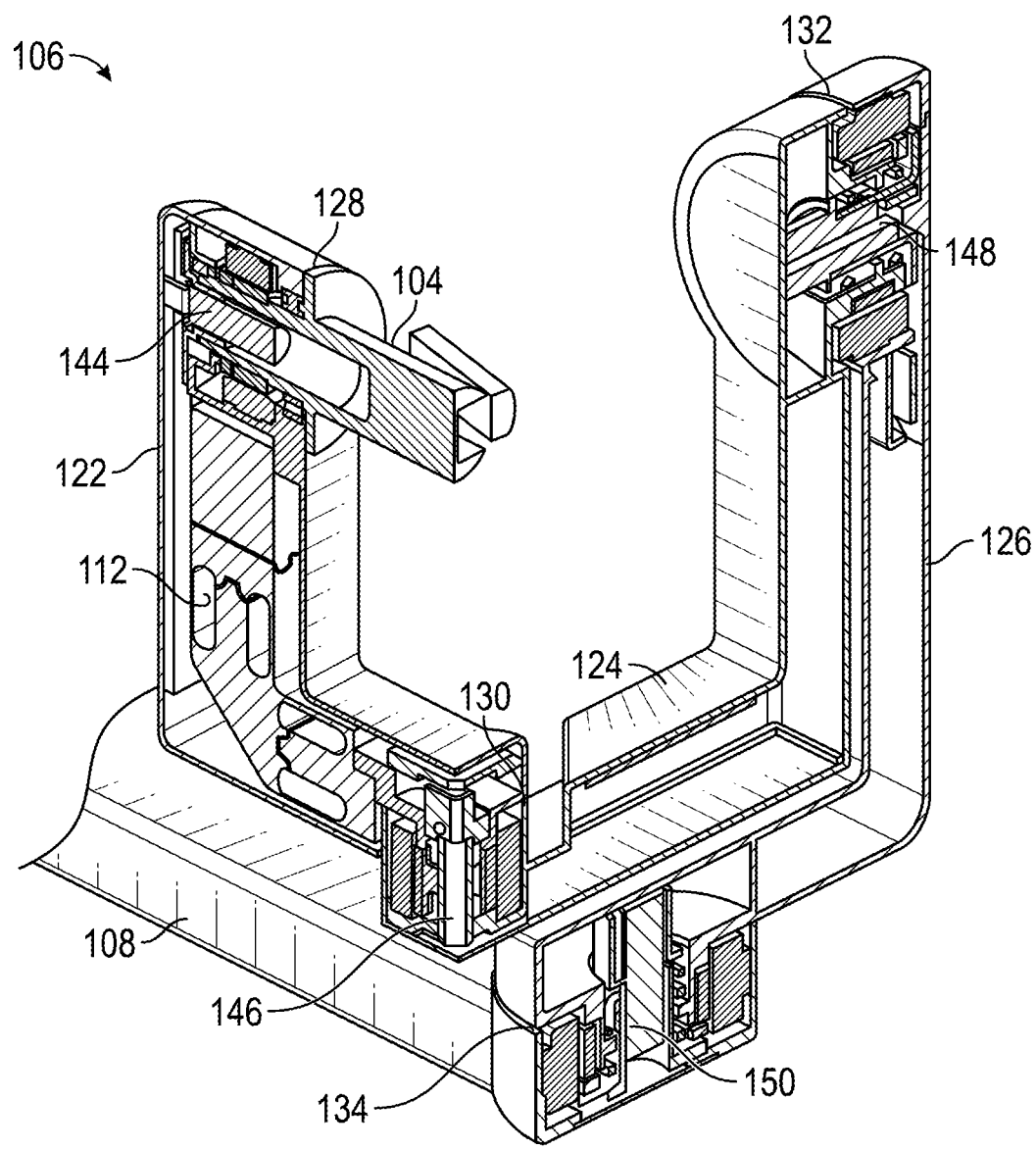
FIG. 18 is an isometric, cross-sectional view of a first embodiment of a gimbal including a load cell in a first position.
Figure 19A:
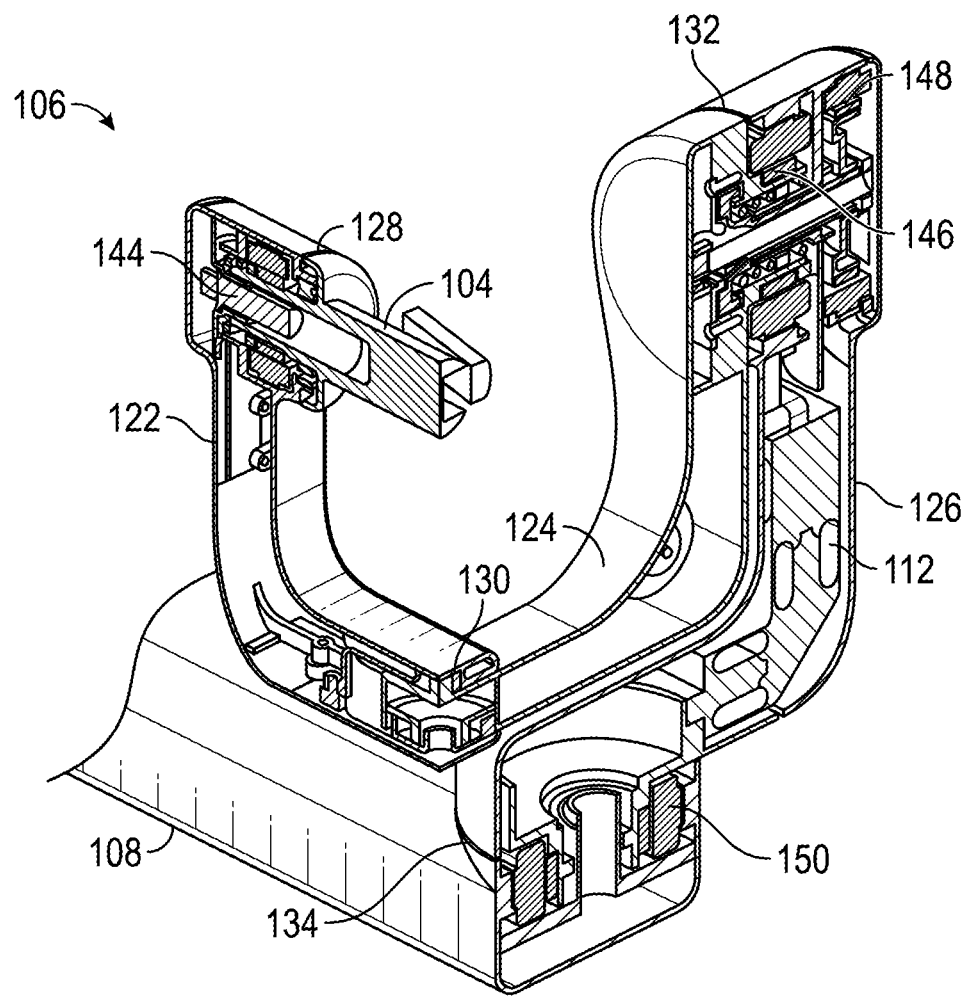
FIG. 19A is an isometric, cross-sectional view of a second embodiment of a gimbal including a load cell in a second position.

In the illustrated embodiment, the load cell 112 is positioned within the gimbal 106. FIGS. 18 and 19A, described below, show two different embodiments of where the load cell 112 can be positioned within the gimbal 106. Other positions for the load cell 112 are also possible. In some embodiments, the load cell 112 is positioned in the positioning platform 108. In some embodiments, more than one load cell 112 is included (e.g., two, three, four, or more load cells), which can be positioned in the handle 104, the gimbal 106, and/or the positioning platform 108.

In some embodiments, the load cell 112 is advantageously positioned distally (closer to the handle 104) in the controller 102. This is because, in some embodiments, the admittance control can be used to hide the perceived mass of the portions of the controller 102 that are located proximally of the load cell 112 (e.g., the portions of the controller 102 that are located on the opposite side of the load cell 112 from the handle 104).

Figure 16C:
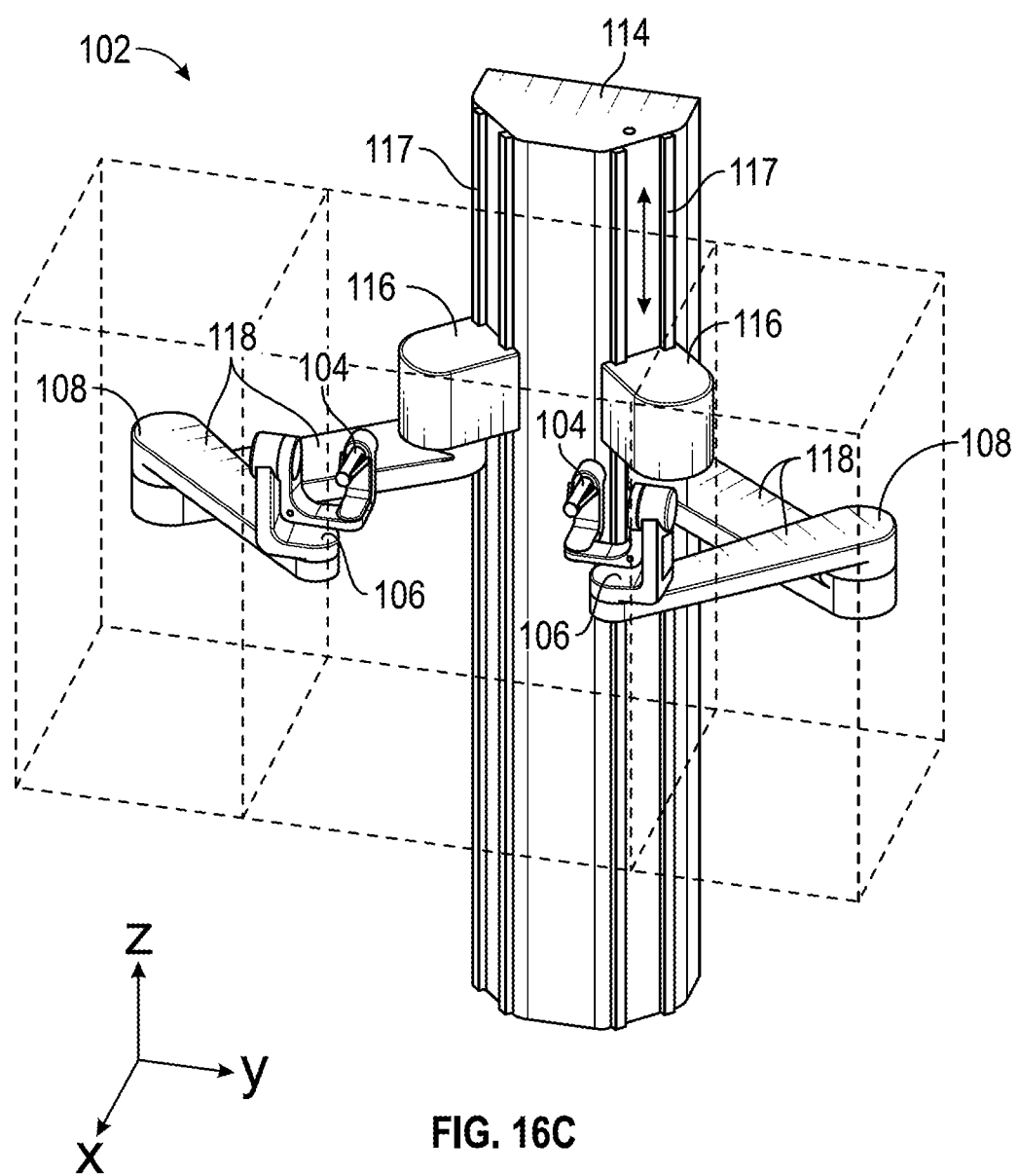
FIG. 16C is an isometric view of an embodiment a controller including two gimbals and a positioning platform.

FIG. 16C is a perspective view of an embodiment of a controller 102. In the illustrated embodiment, the controller 102 is configured to allow manipulation of one or more medical instruments. As illustrated, the controller 102 can include a pair of handles 104. In some embodiments, the pair of handles 104 operates a single instrument, while in other embodiments, each of the pair of handles 104 each operates its own corresponding instrument. Each handle 104 is connected to a gimbal 106. Each gimbal is connected to a positioning platform 108. In some embodiments, the handle 104 is considered distal from the gimbal 106, which is considered distal to the positioning platform 108. The handle 104 and gimbal 106 are shown in greater detail in FIG. 17 and will be described below.

As shown in FIG. 16C, in the illustrated embodiment, each positioning platform 108 includes a SCARA (selective compliance assembly robot arm) arm 118 having a plurality of links coupled to a column 114 by a prismatic joint 116. The prismatic joints 116 are configured to translate along the column 114 (e.g., along rails 117) to allow the handle 104 to be translated in the z-direction, providing a first degree of freedom. The SCARA arm 118 is configured to allow motion of the handle 104 in an x-y plane, providing two additional degrees of freedom. Thus, each of the positioning platforms 108 illustrated in FIG. 16C are configured to provide three degrees of positional or translational freedom and allow the operator to position the handles 104 at any position (within reach of the positioning platform) in three dimensional (e.g., x, y, z) space.

In some embodiments, the column 114 (and rails 117) extends along an axis that is aligned with the vertical direction (e.g., the z-direction as illustrated) of the workspace, which can be aligned with the direction of gravity. An advantage of this positioning platform 108 is that it can provide for gravity compensation. In other words, the prismatic joint 116 of the positioning platform 108 can maintain a constant orientation of the gimbal 106 relative to the forces of gravity.

In some embodiments, the positioning platform 108 can have other configurations. For example, the positioning platform 108 need not include a prismatic joint and/or a SCARA arm in all embodiments.

In some embodiments, a load cell 112 (not shown in FIG. 16C) can be provided in a portion of the controller 102 (e.g., such as in the gimbal 106). The addition of the load cell 112 enables the controller to have admittance control in addition to impedance control. Under admittance control, the perceived inertia of the controller 102 can be reduced. This is because mass of the gimbal 106 and/or positioning platform can be hidden via the load cell 112. This can be because the load cell 112 can measure the forces imparted on the controller and be used to provide outputs that drive motors in the controller 102 to assist with the motion of the controller 102. The amount of mass that is hidden depends on the location of the load cell 112. In some embodiments, mass that is proximal to the load cell 112 can be partly or substantially hidden, while mass that is distal to the load cell 112 will not be hidden In some embodiments, by positioning the load cell 112 distally on the controller 102 (e.g., in the gimbal 106 shown in FIG. 16C), the mass of the gimbal 106 can be partially or substantially hidden while operating the controller 102. Likewise, the mass of the positioning platform 108 (which has a relatively higher mass than the gimbal 106) can also be partially or substantially hidden while operating the controller 102. The hidden mass advantageously results in a lower perceived inertia by a clinician. Without the load cell 112, in order to move the handle 104 in the z-direction, the operator would have to supply sufficient force to the handle 104 to lift the handle 104, the gimbal 106, and the SCARA arm 118 upward. Further, one can envision that it would require less force to move the handle in the x-y plane than to move in the z-direction. This disparity would likely result in an uneven operating experience for the operator that would make the controller 102 difficult to use. Thus, by including a load cell 112, as described herein, the controller 102 can assist the user in translating the handle 104 in the x-, y-, and z-directions and provide a much more even and controlled operating experience. In some embodiments, the load cell 112 enables the positioning platform 108 to operate substantially or completely under admittance control. In contrast with the positioning platform 108, the moment of inertia of the gimbal 106 can be relatively lower. This can be because the gimbal 106 is generally much smaller than the positioning platform 108. Because of this, at least some portions of the gimbal 106 can be suitable for impedance control.

One advantage of such a hybrid impedance/admittance controller 102 as described herein is that the perceived inertia of the system can be relatively lower than systems that rely fully on impedance control. Further, the mechanical structure of the hybrid controller 102 can be simpler because the admittance control can be used to supplement and even out the movement of the system. In contrast, the mechanical structure of impedance only systems is often very complex in an effort to normalize the forces required to move the systems in the different directions and minimize perceived inertia.

In some embodiments, by using a hybrid controller 102 as described herein, it is possible that the mass and inertia of the gimbal 106 can actually be increased relative to the gimbals of impedance only controllers because so much of the total mass and inertia of the controller 102 can be hidden by the admittance control of the positioning platform. Increasing the size of the gimbal can, in some embodiments, allow for use of larger motors, which can allow the controller to provide stronger haptic feedback forces when compared to other systems, which necessitate the use of lightweight gimbals and motors to avoid increasing the overall mass and inertia.

As shown in FIG. 16C, the hybrid controller 102 can be viewed as a plurality of links and joints in series, e.g., as a serial link manipulator. The handle 104, the gimbal 106 and the positioning platform 108 each comprise one or more links operably coupled, with the most proximal link being adjacent the column 114 of the positioning platform 108 and the most distal link being part of the handle 104 itself. In some embodiments, one or more load cells 112 (not shown in FIG. 16C) can be inserted into the controller 102 to provide admittance control of at least some portions of the controller 102. Other portions of the controller 102 can be controlled by impedance control (or in some instances, passive control) by a clinician or operator. In some embodiments, links and joints that are proximal to the load cell 112 may be directly or indirectly affected by the load cell 112. Manipulation of these proximal links and joints can thus be assisted with admittance control. In some embodiments, links and joints that are distal to the load cell 112 may not be affected, either directly or indirectly, by the load cell 112. Manipulation of these distal links and joints can thus be assisted with impedance control. For example, in the embodiment in FIG. 19A (which is discussed in more detail below), a load cell 112 is positioned in the gimbal 106 such that distal joints 128, 130, 132 (shown in FIG. 17) may not be affected directly or indirectly by the load cell 112. In other words, the manipulation of the axes of the gimbal 106 at these joints is not based on the output of the load cell 112 directly or indirectly. These distal links and joints can be moved by impedance control. In contrast, links and joints that are proximal to the load cell 112 (such as those in the positioning platform 108) may be affected directly or indirectly by the load cell 112. In other words, the manipulation of the axes at these joints is based on the output of the load cell 112 directly or indirectly. These proximal links and joints can be moved by admittance control.

B. Examples of Load Cell Positioning

As mentioned above, in some embodiments, the load cell 112 (or force sensor) is positioned in the gimbal 106. In some embodiments, the gimbal 106 provides the rotational degrees of freedom for the controller 102 with impedance control, while the positioning platform 108 can provide the positional degrees of freedom for the controller 102 with admittance control (e.g., based on the output of the load cell 112 positioned in the gimbal 106). There are many ways the load cell 112 can be positioned within the gimbal 106. The degree that a perceived inertia of a controller 102 is reduced can be based in part on the location of the load cell 112 within the gimbal 106. Two example embodiments showing a load cell 112 positioned in two different portions of a gimbal 106 are described in this section. Other embodiments are also possible.

Figure 17:
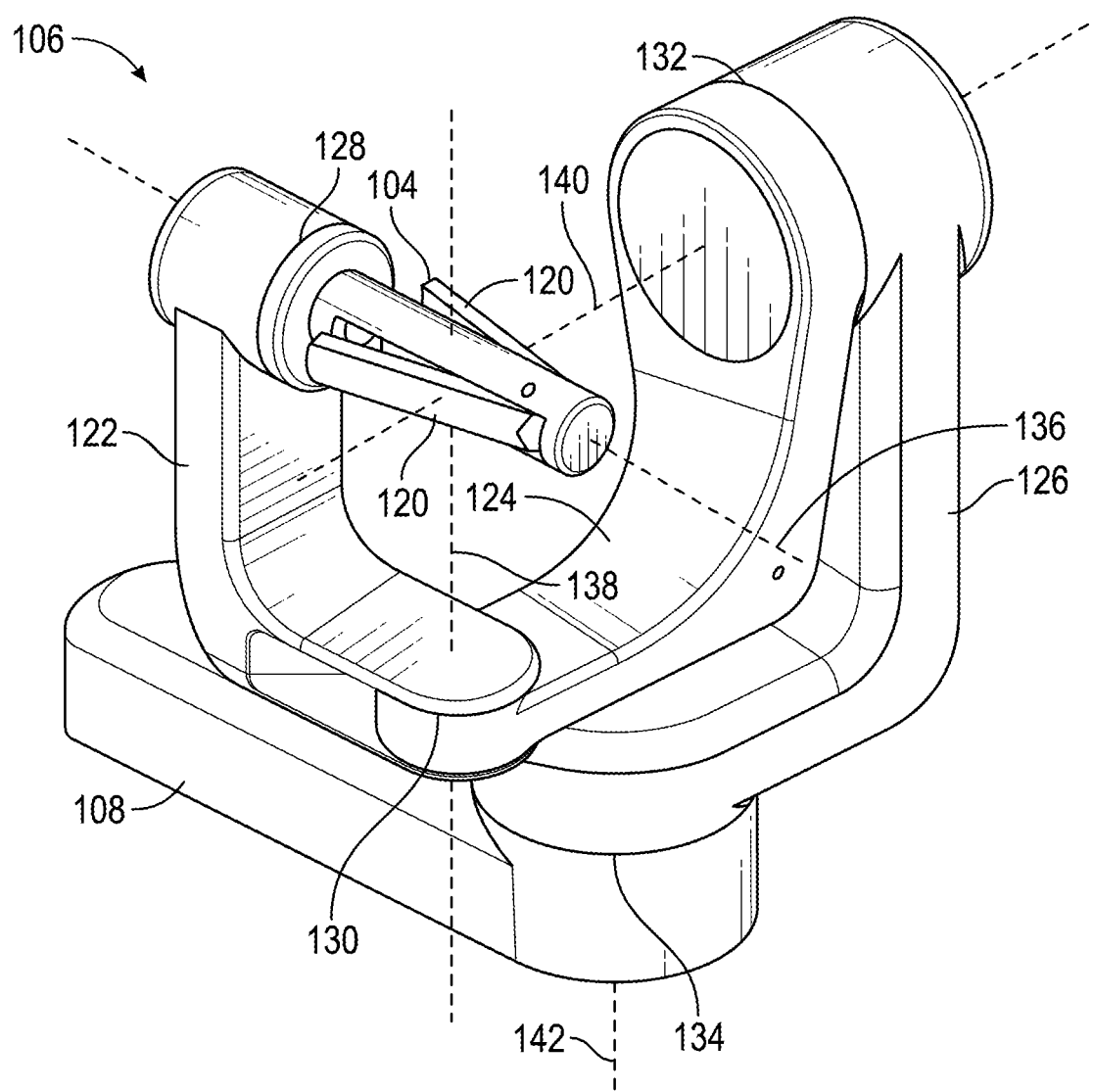
FIG. 17 is an isometric view of an embodiment of a gimbal for a controller.

FIG. 17 is an isometric view of an embodiment of a gimbal 106. As illustrated, for some embodiments, the gimbal 106 is positioned at the distal end of the positioning platform 108 (only the last link of the positioning platform 108 is illustrated in FIG. 17). As used in this application, in the context of the controller 102, the term distal refers to a direction toward the handle 104 (e.g., the handle 104 is the distal-most component of the controller 102) and the term proximal refers to the opposite direction (e.g., toward the column 114, see FIG. 16C). Accordingly, a proximal end of the gimbal 106 can be attached to the distal end of the positioning platform 108. Further, the handle 104 can be positioned at the distal end of the gimbal 106.

In some embodiments, the handle 104 is configured to be held by the operator. The handle 104 can be configured to simulate or mimic the medical instrument that the controller 102 is used to control. In some embodiments, the handle comprises a grasper handle (e.g., a radially symmetric grasper handle), a stylus, a paddle-type handle, etc. In the illustrated embodiment, the handle 104 includes two actuation arms 120 configured to provide the instrument actuation degree of freedom discussed above. While holding the handle 104, the operator can adjust an angle between the actuation arms 120 to control a corresponding angle associated with the controlled medical instrument. For example, in a case where the medical instrument is a grasper, shears, etc., the angle between the actuation arms 120 can be used to control the angle between two jaws of the grasper.

In the illustrated embodiment, the gimbal 106 comprises three arms or links connected by joints. Arranged distally to proximally and as illustrated in FIG. 17, the gimbal 106 comprises a first link 122, a second link 124, and a third link 126. Arranged distally to proximally and as illustrated in FIG. 17, the gimbal 106 also comprises a first joint 128, a second joint 130, a third joint 132, and a fourth joint 134. The joints allow the various links to rotate, providing the gimbal 106 with the rotational degrees of freedom discussed above.

The handle 104 is connected to the distal end of the first link 122 by the first joint 128. The first joint 128 can be configured to allow the handle 104 to rotate relative to the first link 122. In the illustrated embodiment, the first joint 128 allows the handle 104 to rotate around a roll axis 136. In some embodiments, the roll axis 136 is aligned with a longitudinal axis of the handle 104. The first joint 128 can be a revolute joint.

The proximal end of the first link 122 is connected to the distal end of the second link 124 by the second joint 130. The second joint 130 can be configured to allow the handle 104 and the first link 122 to rotate relative to the second link 124. In the illustrated embodiment, the second joint 130 allows the handle 104 and the first link 122 to rotate around a yaw axis 138. In some embodiments, the yaw axis 138 extends through the second joint 130 and intersects with the roll axis 136 at a center point of the handle 104. The second joint 130 can be a revolute joint. As shown, for some embodiments, the first link 122 comprises an L-shape. In some embodiments the first link 122 is configured to have a recess formed therein for receiving the second link 124 and to permit the second link 124 to rotate relative to the first link 122.

The proximal end of the second link 124 is connected to the distal end of the third link 126 by the third joint 132. The third joint 132 can be configured to allow the handle 104, the first link 122, and the second link 124 to rotate relative to the third link 126. In the illustrated embodiment, the third joint 132 allows the handle 104, the first link 122, and the second link 124 to rotate around a pitch axis 140. In some embodiments, the pitch axis 140 extends through the third joint 132 and intersects with the roll axis 136 and the yaw axis 138 at the center point of the handle 104. The third joint 132 can be a revolute joint. As shown, for some embodiments, the second link 124 comprises an L-shape. In some embodiments, the L-shaped second link 124 is received in a recess of the L-shaped first link 122 (as shown in FIG. 17). In other embodiments, the L-shaped first link 122 can be received in a recess of the L-shaped second link 124.

In the illustrated embodiment, the first joint 128, the first link 122, the second joint 130, the second link 124, and the third joint 132 provide three rotational degrees of freedom allowing the rotation of the handle 104 to be adjusted in pitch, roll, and yaw. In the illustrated embodiment, the gimbal 106 further includes a third link 126 and fourth joint 134 providing a redundant rotational degree of freedom. This need not be included in all embodiments, but can provide greater mechanical flexibility for the gimbal 106.

As shown, the distal end of the third link 126 is connected to the proximal end of the second link 124 by the third joint 132. The proximal end of the third link 126 is connected to the distal end of the positioning platform 108 by the fourth joint 134. The fourth joint 134 can be configured to allow the handle 104, the first link 122, the second link 124, and the third link 126 to rotate relative to the positioning platform 108. In the illustrated embodiment, the fourth joint 134 allows the handle 104, the first link 122, the second link 124, and the third link 126 to rotate around an axis 142. In some embodiments, the axis 142 is parallel to the yaw axis 138. In some embodiments, the yaw axis 138 and the axis 142 are coaxial, although, as illustrated, this need not be the case in all embodiments. The axis 142 (and the yaw axis 138) can be parallel to the direction of gravity to maintain the orientation of the gimbal relative to the direction of gravity as described above. The fourth joint 134 can be a revolute joint. As shown, for some embodiments, the third link 126 comprises an L-shape.

FIGS. 18 and 19A show two embodiments of the gimbal 106 illustrated with cross-sectional views of the links of the gimbal 106 to show some of the internal structure of the gimbal 106. As will be described in greater detail below, these two embodiments provide examples of where the load cell 112 can be positioned within the gimbal 106. Although two examples are illustrated, other placements for the load cell 112 are possible. In some embodiments, the term load cell 112 can encompass a single load cell or multiple sub-load cells.

FIG. 18 illustrates a cross-sectional view of a first embodiment of the gimbal 106. As shown, in the first embodiment, the load cell 112 is positioned in the first link 122. Stated another way, the load cell 112 is positioned between the first joint 128 and the second joint 130. In the first embodiment of the gimbal 106, the load cell 112 is positioned near the distal end of the controller 102. Specifically, in this embodiment, the load cell 112 is positioned in the distal most link of the gimbal 106, which is the last link of the gimbal 106 before the handle 104. Due to distal positioning of the load cell 112, in this embodiment, there is very little mass distal of the load cell 112. As such, the perceived inertia of a controller 102 including this embodiment of the gimbal 106 can be greatly reduced.

In the illustrated embodiment of FIG. 18, motors associated with the joints are visible. For example, as shown, a first motor 144 is positioned within the first joint 128, a second motor 146 is positioned within the second joint 130, a third motor 148 is positioned within the third joint 132, and a fourth motor 150 is positioned within the fourth joint 134. In some embodiments, the motors can be used to provide haptic feedback through the gimbal 106. In some embodiments, encoders that are co-located with the motors can be configured to provide measurements (e.g., displacement and position) of the movement of the joints for the impedance control of the gimbal 106.

As shown in FIG. 18, the second, third, and fourth motors 146, 148, 150 are all positioned proximally relative to the load cell 112. As such, in some embodiments, the mass of these motors can be hidden such that the perceived inertia can be reduced. In some embodiments, this can allow larger motors to be used, which can provide stronger haptic feedback through the gimbal 106.

FIG. 19A illustrates a cross-sectional view of a second embodiment of the gimbal 106. As shown, in the second embodiment, the load cell 112 is positioned in the third link 126. Stated another way, the load cell 112 is positioned between the third joint 132 and the fourth joint 134. Compared with the first embodiment of the gimbal 106 (FIG. 18), in the second embodiment, the load cell 112 is more proximally positioned. Thus, in the second embodiment, there is more mass distal of the load cell 112 (e.g., the mass of the handle 104, the first link 122, and the second link 124) which can contribute to a higher perceived inertia of the overall system, and thus a controller 102 including the second embodiment of the gimbal 106 can be perceived as heavier (higher perceived inertia) than a controller 102 including the first embodiment of the gimbal 106 (FIG. 18). However, because the second embodiment of the gimbal 106 can be included on a hybrid controller 102 as described above, an overall reduction in perceived inertia is still achieved when compared with other controllers that rely fully on impedance control. Further, in some respects, the second embodiment of the gimbal 106 can provide several unique advantages. For example, the second embodiment of the gimbal 106 reduces the rotational inertia of the gimbal 106 by positioning the load cell 112 in the third link 126. In hybrid controllers, because the gimbal 106 can be impedance controlled, the operator will feel all the rotational inertia of the gimbal 106. Thus, keeping the inertia low can be beneficial for user experience. Additionally, when compared with the first embodiment of FIG. 18, the second embodiment of gimbal 106 can provide a reduced risk of mechanical shorting as discussed in the following section.

In the illustrated embodiment of FIG. 19A, motors associated with the joints are visible. For example, as shown, a first motor 144 is positioned within the first joint 128, a third motor 148 is positioned within the third joint 132, and a fourth motor 150 is positioned within the fourth joint 134. The gimbal 106 also includes a second motor 146 associated with rotation of the second joint 130; however, as shown in FIG. 19A, the second motor 146 is not positioned at the second joint 130. Rather, the second motor 146 can be positioned in the third joint 132 and mechanically connected to the second joint 130. This is best seen in FIG. 19B.

Figure 19B:
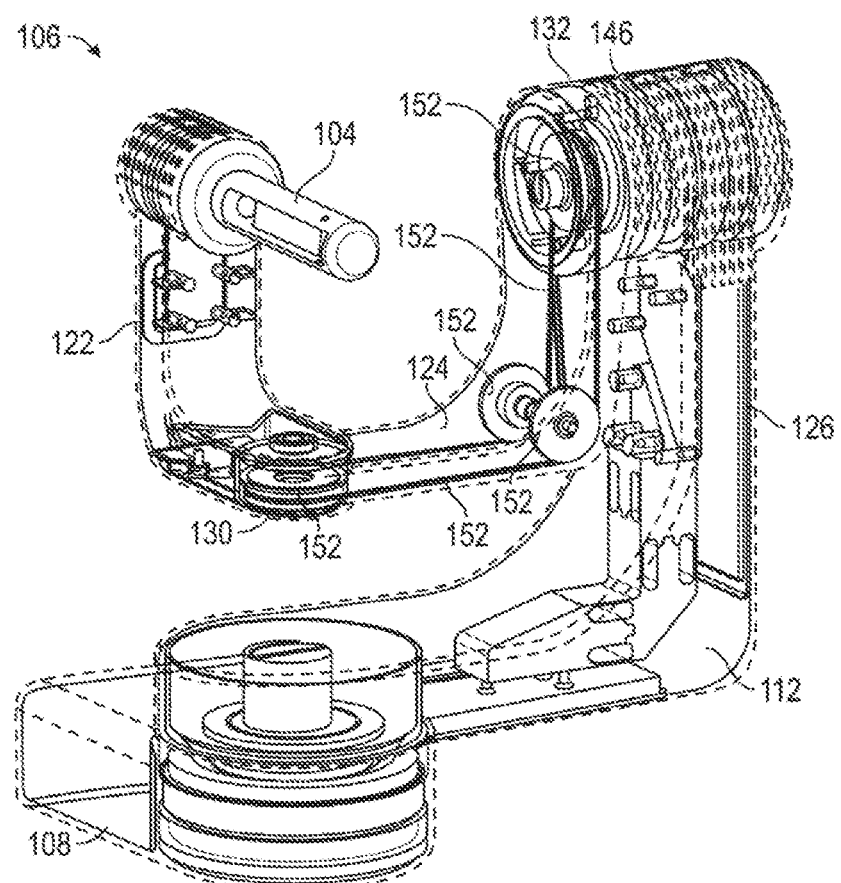
FIG. 19B is an isometric view of the second embodiment of FIG. 19A illustrated with transparent covers to show an embodiment of a cable drive system.

FIG. 19B provides an additional view of the second embodiment of the gimbal 106. In this view, the covers of the links are illustrated as transparent to reveal some of the internal components of the gimbal 106. As shown, the second motor 146 is positioned in the third joint 132 and connected to the second joint 130 by a novel cable drive system 152. The cable drive system 152 advantageously acts as a transmission between the second joint 130 and the second motor 146. The cable drive system can include one or more cables that is routed through one or more cable pulleys in the second link 124 of the gimbal 106.

In this embodiment, the gimbal 106 has an added advantage of having the second joint 130 controlled by a remotely located second motor 146. An advantage of the remotely located second motor 146 is that the motor 146 can be placed near a proximal portion of the gimbal 106, as opposed to near the second joint 130 itself. Positioning the second motor 146 in the third link 126 (as opposed to the second link 124) reduces the rotational inertia of the gimbal. As mentioned above, reducing the rotational inertia can be beneficial because the gimbal 106 is impedance controlled, requiring the user to overcome the inertia of the gimbal 106 to operate the controller.

As before, the motors can be used to provide haptic feedback through the gimbal 106. Further, in some embodiments, the motors can be configured to provide measurements (e.g., displacement and position) of the movement of the joints for the impedance control of the gimbal 106.

Although two embodiments for gimbals 106 including load cells 112 have been described with reference to FIGS. 17-19B, other embodiments are also possible. In other embodiments, gimbals 106 can include two or more load cells 112.

C. Reducing Mechanical Shorting

While the use of hybrid controllers 102 including both impedance and admittance control provides several notable advantages as discussed above (including reducing the perceived inertia of the controllers and providing an improved operating experience), in some embodiments, use of admittance control includes the use of a load cell 112 to measure forces. When implementing embodiments that include a load cell 112, the risk of mechanical shorts should be considered. Mechanical shorts can occur when an operator's hand, wrist, arm or any combination make a rigid or physical bridge between a portion of the controller that is proximal to the load cell 112 and a portion of the controller that is distal to the load cell 112. The effect of a mechanical short can be an unintentional motion that is difficult for the operator to control.

Figure 20A:
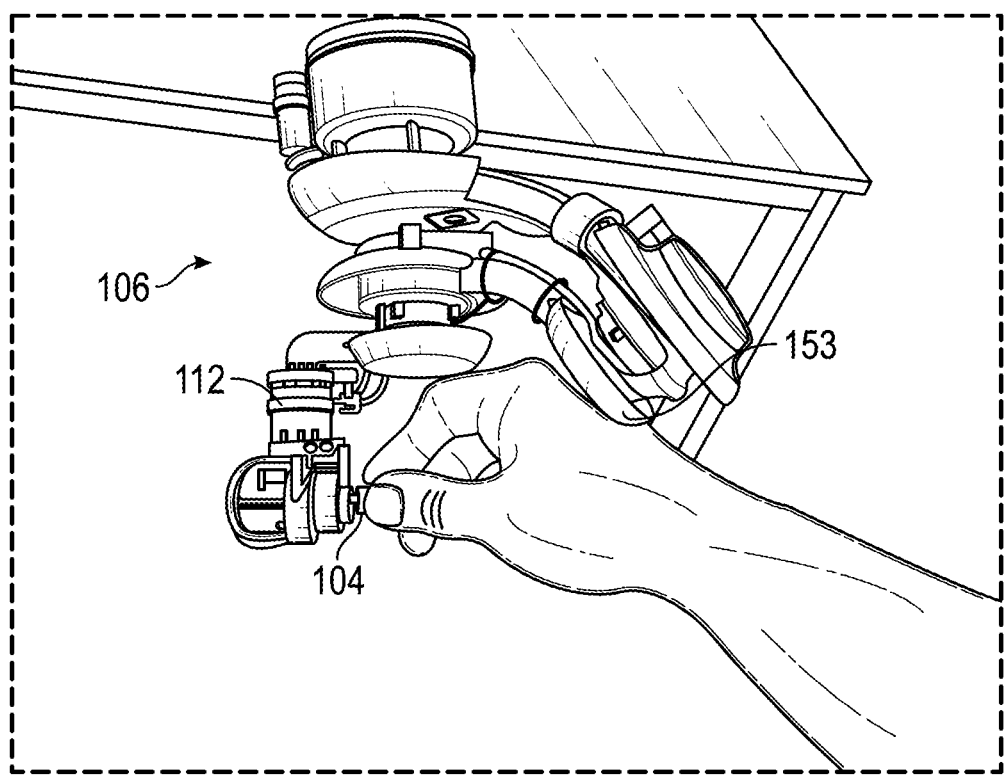
FIG. 20A illustrates an example of a mechanical short.

FIG. 20A is an image illustrating an example of a mechanical short. In the illustrated example, an operator is holding the handle 104 which is distally located of the load cell 112. The operator imparts forces on the handle 104 (e.g., by moving the handle 104) that are measured by the load cell 112 and used for admittance control in the positioning platform (not shown). However, as illustrated, the operator is also contacting a portion 153 of the gimbal that is proximally located relative to the load cell 112 causing a mechanical short. Forces imparted at the portion 153 are also measured by the load cell 112 causing unintentional and uncontrollable motions.

In some embodiments, mechanical shorts create undesirable motions because the systems assume that the operator is imparting all forces at the handle 104, when this is in actuality not true e.g. due to the contact proximal of the load cell 112. Operators can safely contact any portion of the controller or gimbal that is distally located of the load cell 112. Contact with the controller proximal of the load cell 112 can cause the undesirable mechanical shorting.

To reduce the risk of mechanical shorting and increase the portion of the controller that the operator can safely contact without causing a mechanical short, in some embodiments, a shell or cover can be provided over the load cell 112. For example, for a link including the load cell 112, the cover can be attached to the link only distally of the load cell 112 but extend (without contacting) over portions of the link that are located proximal of the load cell 112. Because the cover is only connected distal of the load cell 112, contact with the cover likely will not cause a mechanical short. In some embodiments, the cover can be molded over the underlying components. In other embodiments, the cover can be a slip formed over the underlying components.

Figure 20B:
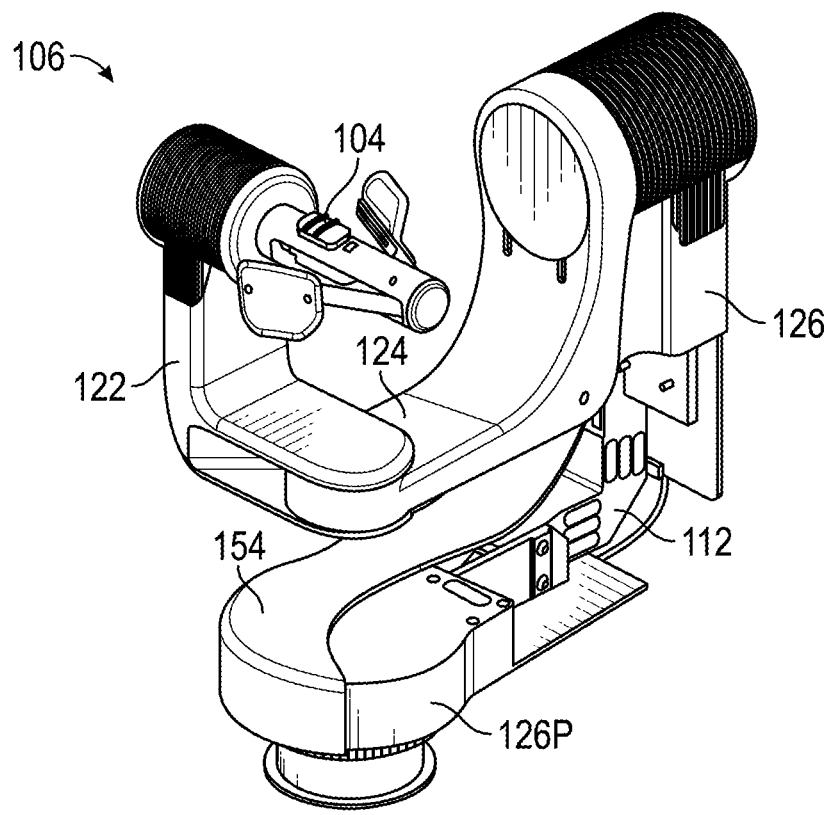
FIG. 20B illustrates an example of a cover for a gimbal configured to reduce the likelihood of a mechanical short.

FIG. 20B illustrates an embodiment of the second embodiment of the gimbal 106 (e.g., as shown in FIGS. 19A and 19B) showing a cutaway version of a cover 154 of the third link 126, which includes the load cell 112. As shown, the load cell 112 is positioned within the third link 126. As such, a portion of the third link 126 is positioned distal of the load cell 112 and a portion 126P of the third link 126 is positioned proximal of the load cell 112. Contact with the proximal portion 126P of the third link 126 would cause a mechanical short. To reduce the likelihood of a mechanical short, the cover 154 extends over and covers the proximal portion 126P. A similar cover can be implemented on the first link 122 for the first embodiment of the gimbal 106 (FIG. 18).

Figure 20C:
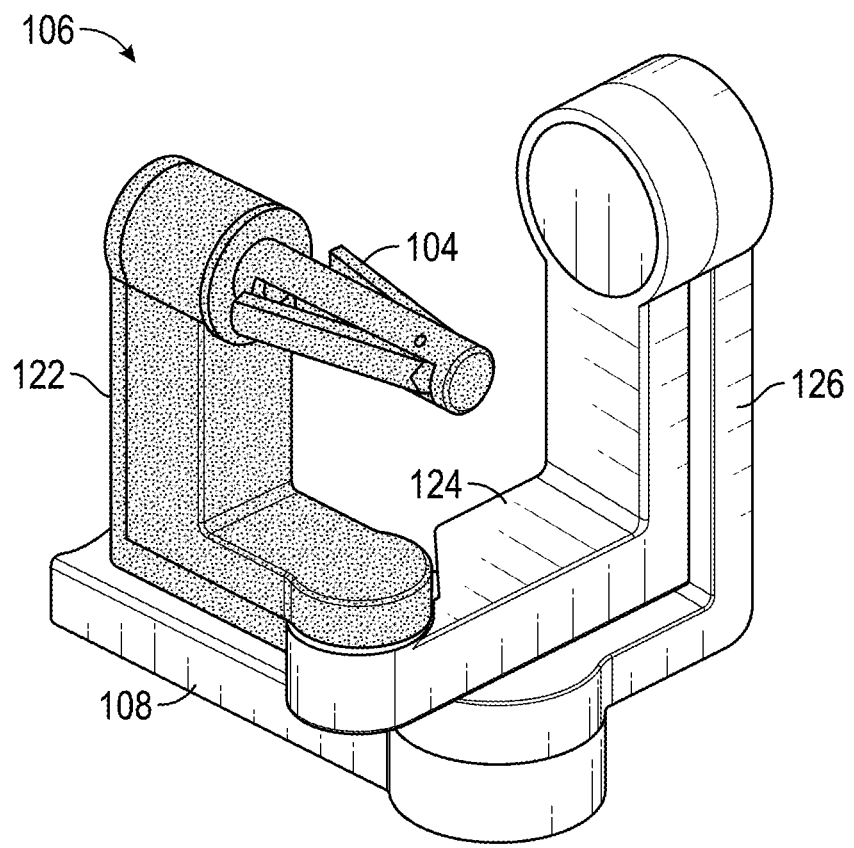
FIG. 20C illustrates the extent of the cover in the first embodiment of the gimbal of FIG. 18 that can be contacted without causing a mechanical short, according to an embodiment.
Figure 20D:
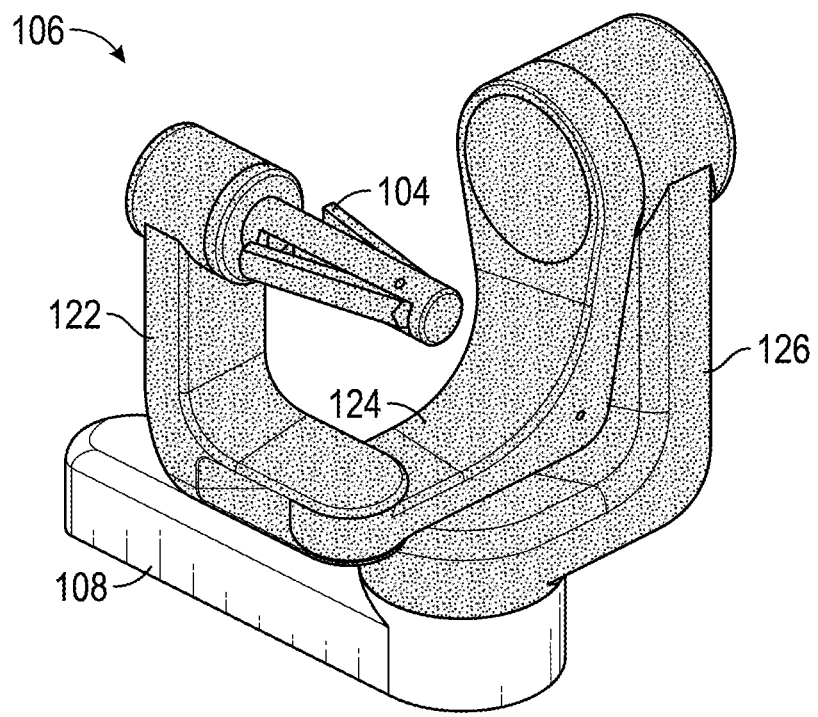
FIG. 20D illustrates the extent of the cover in the second embodiment of the gimbal of FIGS. 19A and 19B that can be contacted without causing a mechanical short, according to an embodiment.
Figure 21:
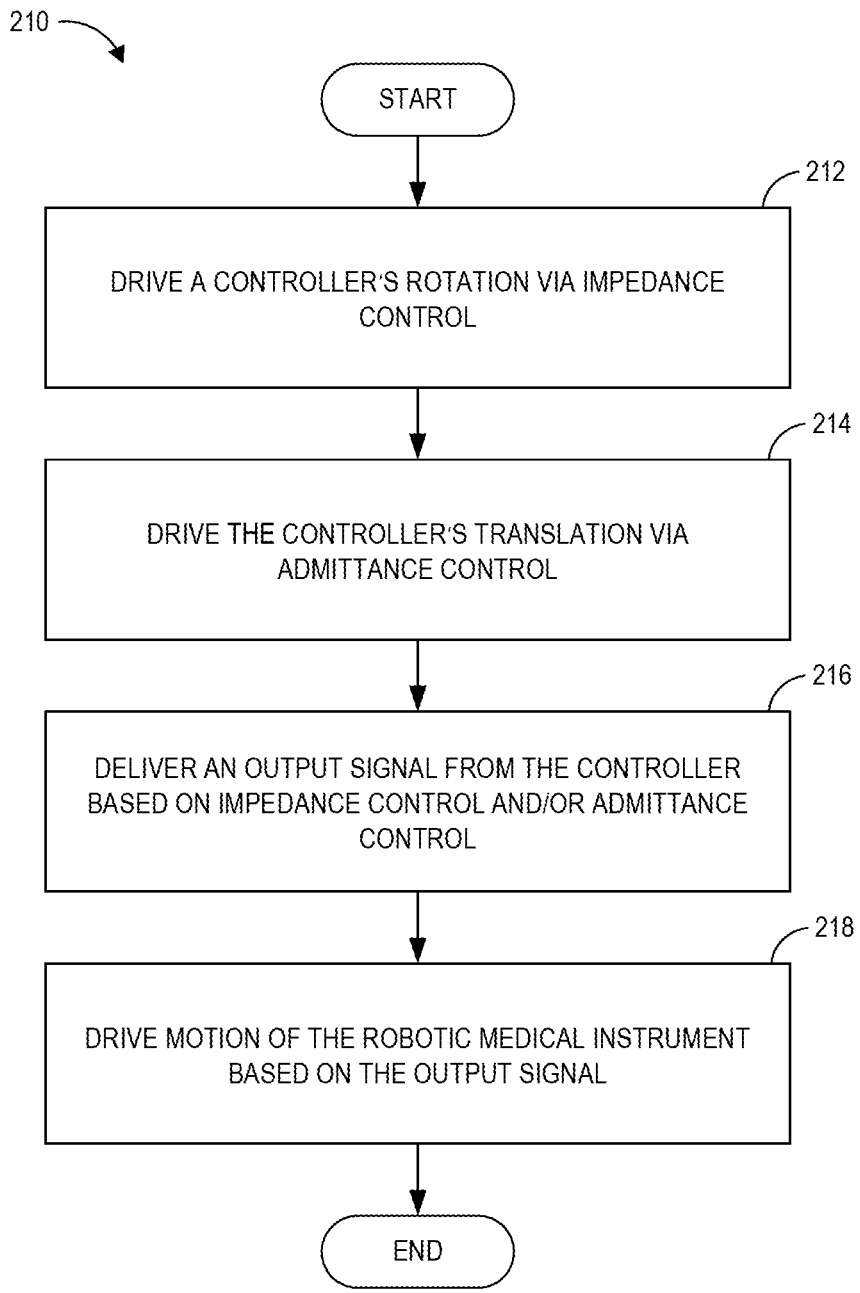
FIG. 21 is a flow chart illustrating an embodiment of a controller method.

FIGS. 20C and 20D illustrate portions of the first embodiment and second embodiment of the gimbal 106 (shown respectively in FIGS. 18 and 19A) that can be contacted without causing a mechanical short. In these figures, the darker shaded portions can be contacted without causing a mechanical short. As shown in FIG. 20C, in the first embodiment of the gimbal 106, the handle 104 and the first link 122 can be contacted without causing a mechanical short. This can be because a cover can extend over the first link 122, which includes the load cell 112. As shown in FIG. 20D, in the second embodiment of the gimbal 106, the handle 104, the first link 122, the second link 124, and the third link 126 can be contacted without causing a mechanical short. This can be because a cover can extend over the third link 123, which includes the load cell 112. Comparing FIGS. 20C and 201D, the second embodiment (FIG. 20D) can offer a greater area of protection against mechanical shorts than the first embodiment (FIG. 20C). This can reflect a tradeoff between the two designs. While the first embodiment (FIG. 20D) can be perceived as lighter (because the load cell 112 is positioned close to a distal link of the gimbal), it can also have more area that can be subject to shorting. In contrast, while the second embodiment (FIG. 20D) can be perceived as heavier (because the load cell 112 is positioned close to a proximal link of the gimbal), it can have an area that is more protected from shorting. Regardless, both of these designs provide controllers that are perceived lighter than those that rely solely on impedance control, and have novel covers that protect against the risk of mechanical shorts. Those of skill in the art will appreciate that both embodiments offer particular advantages and may be suitable for use in various situations.

D. Example Controller Methods 21 is a flow chart illustrating an example method 210 in which a controller (e.g., a master) controls a medical instrument (e.g., a slave). The method 210 can be configured for hybrid control, using both impedance and admittance control. Although illustrated sequentially, the blocks of the method 210 can be implanted in other orders or one or more of the block can occur at substantially the same time. The method 210 begins at block 212, in which a user can drive a controller's rotation via impedance control. At block 214, the user can also drive the controller's translation via admittance control. In some embodiments, the admittance control can be enabled via one or more load cells positioned in a gimbal of the controller.

At block 216, an output signal from the controller is delivered via a processor. The output signal can be based on impedance and/or admittance control of the controller. At block 218, motion of the robotic medical instrument is driven based on the output signal.

Figure 22:
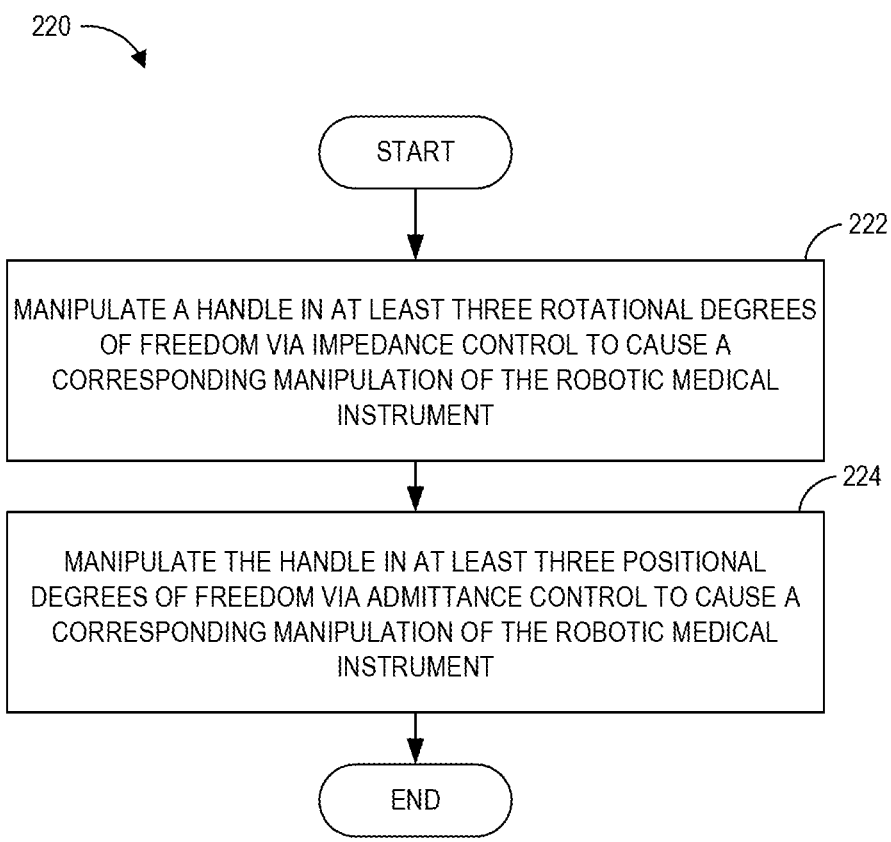
FIG. 22 is a flow chart illustrating another embodiment of a controller method.

FIG. 22 is a flow chart illustrating an example controller method 220. The method 220 can be configured for hybrid control, using both impedance and admittance control. Although illustrated sequentially, the blocks of the method 220 can be implanted in reverse order or can occur at substantially the same time. The method 220 begins at block 222, in which a handle of a controller is manipulated via impedance control to cause a corresponding manipulation of a robotic medical instrument. In some embodiments, the handle is manipulated in one or more rotational degrees of freedom. In some embodiments, the handle is manipulated in at least three rotational degrees of freedom. In some embodiments, the handle is manipulated in at least pitch, roll, and yaw. In some embodiments, manipulating the handle comprises manipulating a gimbal.

At block 224, the handle is manipulated via admittance control to cause corresponding manipulation of the robotic medical instrument. In some embodiments, the handle is manipulated in one or more positional or translational degrees of freedom. In some embodiments, the handle is manipulated in at least three positional or translational degrees of freedom. In some embodiments, the handle is manipulated in at x-, y-, and z-directions. In some embodiments, manipulating the handle comprises manipulating a positioning platform.

E. Hybrid Controllers with Degree of Freedom Constraint

The hybrid controllers described above may generally use an impedance controlled gimbal and an admittance controlled positioning platform. That is, for the hybrid controllers described above, all three rotational degrees of freedom of the gimbal can use impedance control and all three positional degrees of freedom of the positioning platform can use admittance control.

In this section, an additional type of hybrid controller is described that can include an impedance controlled gimbal (e.g., with three rotational degrees of freedom) and a positioning platform that is under admittance control for one degree of freedom (e.g., on the vertical translation axis) and impedance control for the other two degrees of freedom. Accordingly, for this type of hybrid controller there can be a one degree of freedom constraint on the admittance control. That is, admittance control is limited or constrained to only one degree of freedom, such as the vertical translational degree of freedom.

As described here, this can be achieved by providing a one degree of freedom load cell in the gimbal (as opposed to the three degree of freedom load cell 112 described above). A hybrid controller with a degree of freedom constraint can lead to a number of advantages, such as greater stability, robustness, and reduced cost.

In some embodiments, a hybrid controller constrained to only one degree of freedom can include the same or a similar kinematic structure as the controllers 102 described above. For example, the hybrid controller constrained to only one degree of freedom can include a gimbal 106 and positioning platform 108 as shown above, comprising a plurality of links connected by joints. However, for the hybrid controller constrained to only one degree of freedom, the load cell 112 would be a one degree of freedom load cell that measures forces in only a single direction. In some embodiments, the load cell 112 is configured to measure forces in only the direction of gravity, or along an axis of the column 114 (see FIG. 16C).

In an embodiment, the load cell 112 illustrated in FIG. 18 can be a one degree of freedom load cell. In another embodiment, the load cell 112 illustrated in FIGS. 19A and 19B can be a one degree of freedom load cell. In another embodiment, it is possible to place the load cell 112 behind (e.g., proximal of) the fourth joint 134 of the gimbal 106 (see FIGS. 18 and 19A). This embodiment may have increased mass distal of the load cell 112 (when compared with the embodiments described above). In some embodiments, the more mass distal of the load cell 112, and/or the less stiffness of the load cell 112, the lower the mechanical vibrational frequencies introduced, and thus the worse is the admittance control performance and/or stability. By switching to a one degree of freedom load cell 112, this type of hybrid controller has the potential to reduce the packaging size, mass, and cost, while increasing the stiffness, range, and accuracy of the load cell 112, which can result in better admittance performance and/or stability.

In some embodiments, the positioning platform 108 of a hybrid controller with a degree of freedom constraint can be similar to the positioning platform 102 shown in FIG. 16. For example, the positioning platform may include a prismatic base axis aligned with a vertical direction of the workspace. The positioning platform may also include two rotary joints arranged in a SCARA configuration provide planar motion perpendicular to the prismatic joint. In some embodiments, the prismatic axis can be implemented with either a lead-screw actuator or a linear actuator. In some embodiments, use of a linear actuator can move backlash, reduce noise during driving, and have less motor inertia.

Further, in some embodiments, the direct drive current can also be used for more accurate vertical force measurement and/or estimation. To enhance the impedance control on the planar SCARA portion, the motors driving the SCARA portion can be made highly back-drivable. In some embodiments, the motor associated with the elbow of the SCAR can be remotely positioned into the column 114. These improvements can reduce the inertia of planar links of the positioning platform for reduced mass on impedance-controlled planar positioning degrees of freedom.

The mechanical vibrational frequency is enhanced from reduced inertia and the removal or reduction of gearbox compliance, for improved performance and/or stability of vertical admittance control as well. In terms of perceived mass, on the planar degrees of freedom of the positioning platform (e.g., of the SCARA), they are similar and relatively uniform, dominated by the mass of the gimbal. The raw mass along vertical axis can be higher, but admittance control can be tuned to match the perceived mass of the other degrees of freedom for a more uniform performance in the entire workspace. A one degree of freedom load cell 112 can be used to measure the vertical force at the location of prismatic actuation, when the accuracy of current-based force measurement is not sufficient. This information, combined with calibration and gimbal distal force measurement, can estimate additional vertical external force at any point distal to the vertical actuation. Therefore, all mechanical shorts and unexpected collisions can be detected and prevented for enhanced safety.

3. Implementing Systems and Terminology.

Implementations disclosed herein provide systems, methods and apparatus for robotically-enabled medical systems. Various implementations described herein include controllers for the robotically-enabled medical systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "approximately" or "about" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotically-enabled teleoperated system, comprising:
    a controller and a robotic tool capable of manipulation by the controller, wherein the controller comprises:
    a handle configured for actuation by an operator to cause a corresponding manipulation of the robotic tool;
    a gimbal comprising a plurality of joints and a load cell configured to measure a force imparted on the controller and to produce an output signal based on the measured force; the gimbal being physically coupled to the handle and configured to allow manipulation of the handle in multiple degrees of freedom, wherein a first joint of the plurality of joints of the gimbal is configured to be manipulated based on an impedance control such that manipulation of the gimbal causes a corresponding manipulation of the robotic tool based on a displacement of the first joint; and
    a positioning platform physically coupled to the gimbal and configured to allow manipulation of the handle in multiple degrees of freedom, wherein at least a portion of the positioning platform is configured to be manipulated based on an admittance control such that manipulation of the positioning platform causes a corresponding manipulation of the robotic tool based on the force measured by the load cell.

2. The system of claim 1; wherein the robotic tool is a medical instrument.

3. The system of claim 1, wherein the gimbal is coupled to the positioning platform via a rotational joint.

4. The system of claim 1, wherein the gimbal allows manipulation of the handle in at least three rotational degrees of freedom.

5. The system of claim 1, wherein the positioning platform allows manipulation of the handle in at least three positional degrees of freedom.

6. The system of claim 1, further comprising a robotic arm coupled to the robotic tool, and wherein the robotic tool comprises at least one of a catheter, a scope, a grasper, a sealer, or a cutter.

7. The system of claim 1, wherein the load cell is positioned within the gimbal.

8. The system of claim 7, wherein the admittance control provides a perceived inertia to a second joint of the gimbal and the first joint is not affected by the output signal of the load cell.

9. The system of claim 7, wherein the gimbal comprises at least a first link, a second link, and a third link arranged distally to proximally and connected by joints, and wherein the load cell is positioned within the first link.

10. The system of claim 9, wherein the joints are revolute joints.

11. The system of claim 7, wherein the gimbal comprises at least the first joint, a second joint, and a third joint arranged distally to proximally and connected by links, and wherein the load cell is positioned distally of the second joint.

12. The system of claim 7, wherein the gimbal comprises at least a first link, a second link, and a third link arranged distally to proximally and connected by joints, and wherein the load cell is positioned within the third link.

13. The system of claim 7, wherein the gimbal comprises at least the first joint, a second joint, and a third joint arranged distally to proximally and connected by links, and wherein the load cell is positioned proximally of the third joint.

14. The system of claim 7, wherein the gimbal comprises a cover attached to a distal end of the load cell configured to shield structure proximal to the load cell to thereby prevent a mechanical short between the distal end of the load cell and the shielded structure.

15. The system of claim 1, further comprising a motor positioned within the gimbal for controlling a joint of the gimbal.

16. The system of claim 15, wherein the motor is connected to the joint by a cable drive.

17. The system of claim 16, wherein the motor is located proximally of the joint.

18. The system of claim 1, wherein the positioning platform comprises at least one prismatic joint.

19. The system of claim 18, wherein an axis of motion of the prismatic joint is aligned with a direction of gravity.

20. The system of claim 19, wherein the gimbal is coupled to the positioning platform by a joint, and wherein an axis of the joint is aligned with the direction of gravity.

* * * * *